United States Patent
Lozinsky et al.

(10) Patent No.: US 10,085,994 B2
(45) Date of Patent: *Oct. 2, 2018

(54) TOPICAL COMPOSITIONS AND METHODS OF TREATMENT OF TOPICAL DISORDERS

(71) Applicant: PeriTech Pharma Ltd., Herzliya (IL)

(72) Inventors: Evgenia Lozinsky, Beer-Sheva (IL); Eran Eilat, Herzliya (IL)

(73) Assignee: PeriTech Pharma Ltd., Herzliya (IL)

( * ) Notice: Subject to any disclaimer, the term of this patent is extended or adjusted under 35 U.S.C. 154(b) by 271 days.

This patent is subject to a terminal disclaimer.

(21) Appl. No.: 14/203,246

(22) Filed: Mar. 10, 2014

(65) Prior Publication Data

US 2014/0255521 A1 Sep. 11, 2014

Related U.S. Application Data

(60) Provisional application No. 61/775,598, filed on Mar. 10, 2013.

(51) Int. Cl.
| | |
|---|---|
| *A61K 31/5375* | (2006.01) |
| *A61K 31/137* | (2006.01) |
| *A61K 45/06* | (2006.01) |
| *A61K 31/535* | (2006.01) |
| *A61K 9/08* | (2006.01) |
| *A61K 9/00* | (2006.01) |
| *A61K 47/20* | (2006.01) |
| *A61K 47/26* | (2006.01) |
| *A61K 47/34* | (2017.01) |
| *A61K 9/70* | (2006.01) |
| *A61K 9/06* | (2006.01) |
| *A61K 9/107* | (2006.01) |
| *A61K 47/24* | (2006.01) |

(52) U.S. Cl.
CPC ........ *A61K 31/5375* (2013.01); *A61K 9/0014* (2013.01); *A61K 9/0031* (2013.01); *A61K 9/06* (2013.01); *A61K 9/08* (2013.01); *A61K 9/107* (2013.01); *A61K 9/7015* (2013.01); *A61K 31/137* (2013.01); *A61K 31/535* (2013.01); *A61K 45/06* (2013.01); *A61K 47/20* (2013.01); *A61K 47/24* (2013.01); *A61K 47/26* (2013.01); *A61K 47/34* (2013.01)

(58) Field of Classification Search
CPC ............................ A61K 31/5375; A61K 9/0014
USPC ......................................................... 514/159
See application file for complete search history.

(56) References Cited

U.S. PATENT DOCUMENTS

| | | |
|---|---|---|
| 3,527,224 A | 9/1970 | Rabinowitz |
| 3,598,122 A | 8/1971 | Zaffaroni et al. |
| 4,613,498 A | 9/1986 | Crosby |
| 4,626,433 A | 12/1986 | Gros |
| 4,689,338 A | 8/1987 | Gerster |
| 4,797,392 A | 1/1989 | Chernomorsky |
| 4,958,748 A | 9/1990 | Otake |
| 4,987,893 A | 1/1991 | Salamone et al. |
| 5,103,812 A | 4/1992 | Salamone et al. |
| 5,130,124 A | 7/1992 | Merianos et al. |
| 5,166,132 A | 11/1992 | Gordon |
| 5,219,880 A | 6/1993 | Thornfeldt |
| 5,234,914 A | 8/1993 | Gallina |
| 5,482,936 A | 1/1996 | Lindstrom |
| 5,756,747 A | 5/1998 | Gerster |
| 5,869,600 A | 2/1999 | Causton et al. |
| 6,074,652 A * | 6/2000 | Ishiwatari ................ A61K 8/06 424/401 |
| 6,110,929 A | 8/2000 | Gerster et al. |
| 6,383,502 B1 | 5/2002 | Dunshee et al. |
| 6,387,405 B1 | 5/2002 | Shah et al. |
| 6,541,485 B1 | 4/2003 | Crooks et al. |
| 5,627,216 A1 | 9/2003 | Brandt et al. |
| 6,756,382 B2 | 6/2004 | Coleman et al. |
| 6,821,523 B2 | 11/2004 | Maibach et al. |
| 7,318,937 B2 | 1/2008 | John et al. |
| 7,642,225 B2 | 1/2010 | Paul et al. |
| 7,879,316 B2 | 2/2011 | Ferrari et al. |
| 7,879,346 B2 | 2/2011 | Lee et al. |

(Continued)

FOREIGN PATENT DOCUMENTS

| | | |
|---|---|---|
| RU | 2277926 C2 | 6/2006 |
| RU | 2440093 C2 | 1/2012 |

(Continued)

OTHER PUBLICATIONS

U.S. Appl. No. 14/203,295, filed Mar. 10, 2014, Topical Compositions and Methods of Treatment of Anorectal Disorders.
U.S. Appl. No. 14/203,329, filed Mar. 10, 2014, Topical Compositions and Methods of Treatment of Anorectal and Genital Disorders.
Tomi, N., "A liquid-film forming acrylate cream for the treatment of anal pruritus", Br. J. Nurs. Jan. 26-Feb. 8, 2012, 21(2):98, 100-102 (Abstract), http://www.ncbi.nlm.nih.gov/pubmed/22306640.
Klykken, Paal et al., "Silicone Film—Forming Technologies for Health Care Applications", Dow Corning (2004), www.dowcorning.com.

(Continued)

*Primary Examiner* — Melenie L Gordon
*Assistant Examiner* — Taina D Matos Negron
(74) *Attorney, Agent, or Firm* — Greenberg Traurig, LLP

(57) ABSTRACT

A topical composition includes at least one film forming ingredient; at least one surfactant; at least one non-polar volatile siloxane solvent; at least 15% (w/w) water; and a therapeutically effective concentration of at least one pharmaceutical agent, wherein the composition is sufficiently designed to dry within 60 seconds after application to a body surface to form a dried composition, and wherein the dried composition forms: a flexible film, wherein the flexible film closely follows irregularities of the body surface as well as movement of the body surface, and (ii) a durable film, wherein the durable film does not crack or flake off and remains intact for more than 12 hours giving release of the pharmaceutical agent for an extended period of time.

23 Claims, 5 Drawing Sheets

(56) References Cited

U.S. PATENT DOCUMENTS

| | | |
|---|---|---|
| 2001/0019721 A1 | 9/2001 | Brandt et al. |
| 2002/0034489 A1 | 3/2002 | Wiegland et al. |
| 2002/0192273 A1 | 12/2002 | Buseman et al. |
| 2004/0265344 A1 | 12/2004 | Zolotariov et al. |
| 2005/0244342 A1 | 11/2005 | Friedman et al. |
| 2006/0004094 A1* | 1/2006 | Agisim ............... A61K 31/137 514/537 |
| 2006/0105028 A1 | 5/2006 | Zhang et al. |
| 2006/0110415 A1 | 5/2006 | Gupta |
| 2007/0044810 A1 | 3/2007 | Ramirez et al. |
| 2008/0014252 A1* | 1/2008 | DelPrete ............. A61K 9/0014 424/449 |
| 2008/0295960 A1 | 12/2008 | Schalau, II et al. |
| 2009/0041680 A1 | 2/2009 | Tamarkin et al. |
| 2009/0047226 A1 | 2/2009 | Teckenbrock et al. |
| 2009/0110415 A1* | 4/2009 | Roof ................. G03G 15/2028 399/33 |
| 2010/0323042 A1* | 12/2010 | Collins ................ A61K 8/347 424/735 |
| 2012/0269748 A1 | 10/2012 | Tamura et al. |
| 2014/0255521 A1 | 9/2014 | Lozinsky et al. |
| 2014/0255522 A1 | 9/2014 | Lozinsky et al. |
| 2014/0256688 A1 | 9/2014 | Lozinsky et al. |
| 2015/0231300 A1 | 8/2015 | Lozinsky et al. |
| 2015/0272957 A1 | 10/2015 | Lozinsky et al. |
| 2015/0366798 A1 | 12/2015 | Lozinsky et al. |

FOREIGN PATENT DOCUMENTS

| | | |
|---|---|---|
| WO | 1999043297 A2 | 9/1999 |
| WO | 2003059320 A1 | 7/2003 |
| WO | WO03059320 * | 7/2003 |
| WO | 2005044232 A1 | 5/2005 |
| WO | 2006101955 A2 | 9/2006 |
| WO | 2011003054 A2 | 1/2011 |
| WO | 2011049247 A1 | 4/2011 |
| WO | 2014164703 A1 | 5/2014 |

OTHER PUBLICATIONS

Colas, Andre, "Silicones in Pharmaceutical Applications", Dow Corning (1997), www.dowcorning.com.
The Register of Drugs of Russia, RLS Encyclopedia of Drugs, 19th issue, Editor-in-Chief G.L. Vyshkovsky, Moscow: RLS-MEDIA, 2010, 2 pages.
Russian Search Report for Russian Application No. 2015143158 dated Mar. 19, 2018.

* cited by examiner

TOPICAL COMPOSITIONS AND METHODS OF TREATMENT OF TOPICAL DISORDERS

RELATED APPLICATION

This application claims the benefit of and priority to U.S. Provisional Application No. 61/775,598, filed Mar. 10, 2013, which is incorporated herein by reference in its entirety.

BACKGROUND OF THE INVENTION

Topical disorders are widespread and include a number of different conditions of the body surfaces such as the skin, nails and mucous membranes. Topical disorders include various kinds of dermatitis, acne, rosacea, onychomycosis, pityriasis, actinic keratosis, eczema, erythema, urticaria, hemorrhoids, anal fissures, anal pruritus, common warts, genital warts, anal warts, and herpes. Currently, there are a number of topically applied formulations for the treatment of topical conditions, including ointments, creams, gels, lotions, jellies and pastes, foams, sprays and medicated pads.

SUMMARY OF THE INVENTION

Topical compositions and methods of treatment of topical disorders are disclosed herein.

According to aspects illustrated herein, there is provided a topical composition that includes at least one film forming ingredient; at least one surfactant; at least 15% (w/w) water; at least one non-polar volatile siloxane solvent; and a therapeutically effective concentration of at least one pharmaceutical agent, wherein the composition is sufficiently designed to dry within 60 seconds after application to a body surface to form a dried composition, and wherein the dried composition forms: a flexible film, wherein the flexible film closely follows irregularities of the body surface as well as movement of the body surface, and (ii) a durable film, wherein the durable film does not crack or flake off and remains intact for more than 12 hours giving release of the pharmaceutical agent for an extended period of time.

According to aspects illustrated herein, there is provided a topical composition that includes a silicone resin film forming ingredient; at least one surfactant selected from the group consisting of sodium lauryl sulfate, alkyl- and alkoxy dimethicone copolyol, polysorbate and a combination thereof; at least 15% (w/w) water; a non-polar volatile siloxane solvent; and a therapeutically effective concentration of at least one pharmaceutical agent selected from the group consisting of pramoxine, phenylephrine, hydrocortisone, salicylic acid, nitroglycerine, sildenafil, procaine, lidocaine, tetracaine, dibucaine, prilocalne, phenacaine, benzyl alcohol, benzocaine, diperodon, dyclonine, dimethisoquin, epinephrine, tetrahydrozoline hydrochloride, an amphetamine, an antihistamine, methylphenidate, mephedrone, oxymetazoline, pseudoephedrine, psilocybin, ephedrine sulphate, imiquimod, podophyllin, podophylotoxin, fluorouracil, sinecatechins, plant extracts, adapalene, benzoyl peroxide, tazarotene, azelaic acid, clindamycin, acyclovir, penciclovir, famciclovir, docosanol or their salts and combinations thereof, wherein the composition is sufficiently designed to dry within 60 seconds after application to a skin or a mucosal surface to form a dried composition, and wherein the dried composition forms: a flexible film, wherein the flexible film closely follows irregularities of the surface as well as movement of the surface, and (ii) a durable film, wherein the durable film does not crack or flake off and remains intact for more than 12 hours giving release of the pharmaceutical agent for an extended period of time.

According to aspects illustrated herein, there is provided a topical composition that includes from about 10.0% (w/w) to about 30.0% (w/w) of trimethylsiloxysilicate; from about 1.0% (w/w) to about 5.0% (w/w) of at least one surfactant selected from the group consisting of sodium lauryl sulfate, alkyl- and alkoxy-dimethicone copolyol, polysorbate and a combination thereof; from about 30.0% (w/w) to about 75.0% (w/w) of a non-polar volatile siloxane solvent; and from about 0.005% (w/w) to about 25.0% (w/w) of a pharmaceutical agent selected from the group consisting of pramoxine, phenylephrine, hydrocortisone, salicylic acid, nitroglycerine, sildenafil, procaine, lidocaine, tetracaine, dibucaine, prilocalne, phenacaine, benzyl alcohol, benzocaine, diperodon, dyclonine, dimethisoquin, epinephrine, tetrahydrozoline hydrochloride, an amphetamine, an antihistamine, methylphenidate, mephedrone, oxymetazoline, pseudoephedrine, psilocybin, ephedrine sulphate imiquimod, podophyllin, podophylotoxin, fluorouracil, sinecatechins, plant extracts, adapalene, benzoyl peroxide, tazarotene, azelaic acid, clindamycin, acyclovir, penciclovir, famciclovir, docosanol or their salts and combinations thereof, wherein the composition is sufficiently designed to dry within 60 seconds after application to a body surface to form a dried composition, and wherein the dried composition forms: a flexible film, wherein the flexible film closely follows irregularities of the surface as well as movement of the surface, and (ii) a durable film, wherein the durable film does not crack or flake off and remains intact for more than 12 hours giving release of the pharmaceutical agent for an extended period of time.

According to some embodiments, if the topical disorder is anal or genital warts, the pharmaceutical agent to be administered is selected from the group consisting of an immunomodulator, a cytotoxin, an anti-inflammatory agent, and combinations thereof.

According to additional embodiments, the composition for use in treating or preventing anal or genital warts comprises about 4.0% (w/w) to about 5.0% (w/w) imiquimod. Alternatively, the composition comprises about 0.5% (w/w) podophyllotoxin. Further alternatively, the composition comprises about 1.0% (w/w) to about 20% (w/w) salicylic acid, about 0.1% (w/w) to about 10% (w/w) 5-fluorouracil or a combination thereof.

According to some embodiments, if the topical disorder is herpes, the pharmaceutical agent is an antiviral selected from the group consisting of acyclovir, penciclovir, famciclovir, docosanol and combinations thereof.

Herpes is a viral affliction, usually transmitted through sexual contact.

Available topical regimens include penciclovir cream, 1% (applied every 2 hours during waking hours for 4 days) and acyclovir cream, 5% (applied 5 times a day for 4 days). Docosanol, a saturated fatty alcohol, is a safe and effective topical application that has been approved by the United States Food and Drug Administration for herpes labialis in adults with properly functioning immune systems.

All the above treatments are applied topically several times a day which is a disadvantage. Formulating the above pharmaceuticals agents in the compositions of the present invention may lead to improved and speedier healing as well as better patient compliance.

According to a further aspect, the present invention provides a method of preventing or treating an anal or genital disorder comprising applying a composition of the present invention to an anal or genital region of a subject in need of such treatment, thereby preventing or treating the anal or genital disorder.

According to aspects illustrated herein, there are provided topical compositions that include at least one flexible film forming ingredient, at least one surfactant, at least one non-polar volatile siloxane solvent, and a therapeutically effective concentration of at least one pharmaceutical agent, wherein the composition is sufficiently designed to dry within 60 seconds after application to a topical surface to form a dried composition, and wherein the dried composition forms: (i) a flexible film, wherein the flexible film closely follows irregularities of the surface as well as movement of the surface, and (ii) a durable film, wherein the durable film does not crack or flake off and remains intact for more than 12 hours giving release of the pharmaceutical agent for an extended period of time.

According to aspects illustrated herein, there is provided a method of preventing or treating a topical disorder that includes topically applying, once daily to a body surface of a subject in need of such treatment, a therapeutically effective amount of a topical composition of the present invention.

According to aspects illustrated herein, there is provided a method of preventing or treating a topical disorder that includes topically applying, once every other day or twice weekly to a body surface of a subject in need of such treatment, a therapeutically effective concentration of a topical composition of the present invention.

The above methods of preventing or treating a topical disorder achieve a similar or better therapeutic effect than commercially available compositions comprising the same active ingredient(s) in the same concentrations wherein applied several times daily.

The topical disorders treated with the compositions of the present invention include, but are not limited to, hemorrhoids, anal fissures, anal cracks, anal fistulas, anal abscesses, anal pruritus, other local anorectal lesions, dermatitis, acne, rosacea, onychomycosis, pityriasis, actinic keratosis, eczema, erythema, urticaria, common warts, genital warts, anal warts, herpes and many others.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

Figure 1:
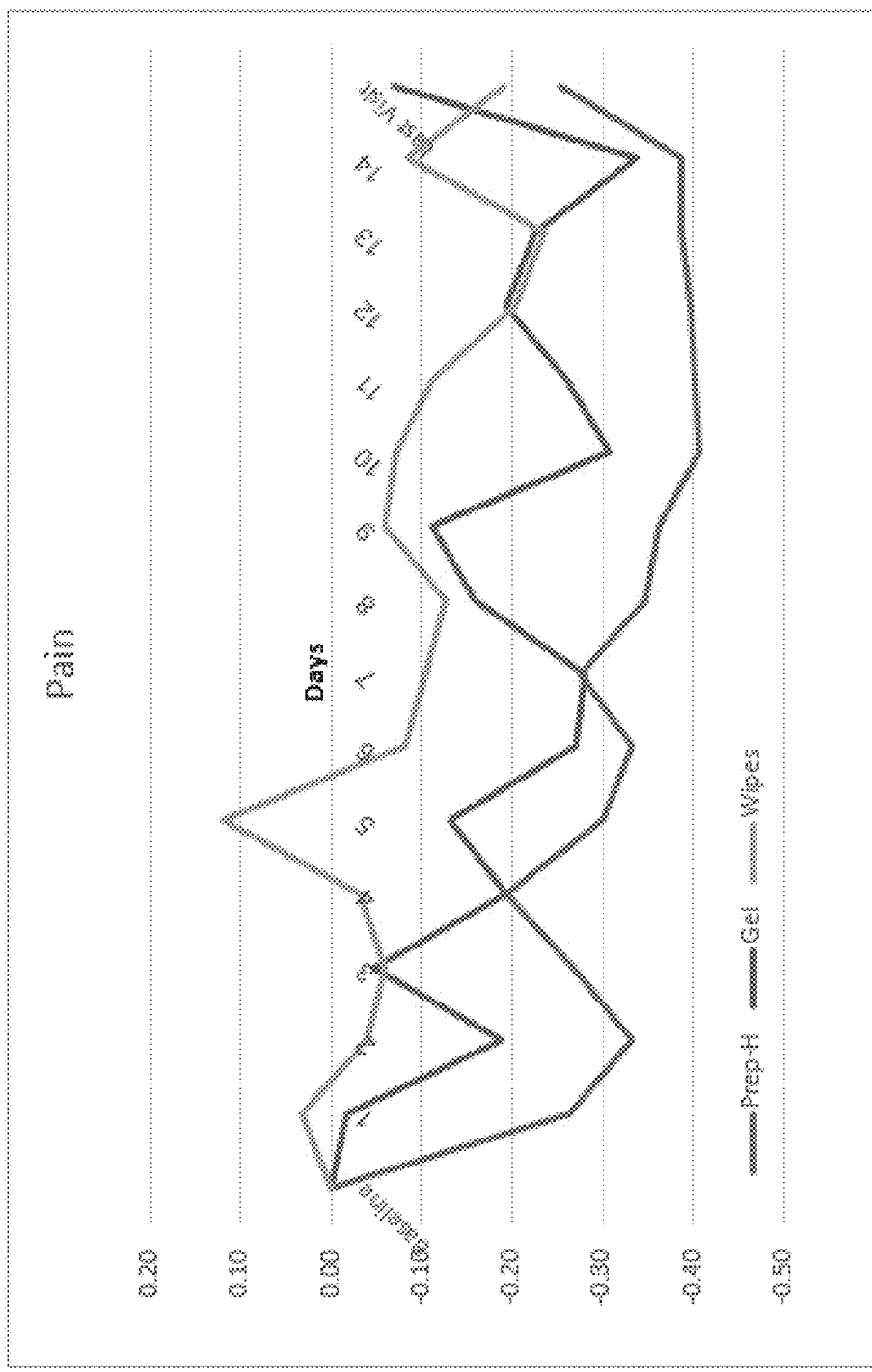
FIG. 1 shows hemorrhoidal pain level after treatment with compositions of the present invention as gel and wipes, as compared to Preparation H. The data presented are the delta meaning the change from the previous day for each parameter measured.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides topical compositions comprising active pharmaceutical agents and uses thereof for treating topical disorders, including, but not limited to, hemorrhoids, anal fissures, anal cracks, anal fistulas, anal abscesses, anal pruritus and other local anorectal lesions, dermatitis, acne, rosacea, onychomycosis, pityriasis, actinic keratosis, eczema, erythema, urticaria, common warts, genital warts, anal warts and herpes.

The topical compositions of the present invention are applied to a body surface for the treatment of topical disorders. Topical formulations currently available for use in the treatment of topical disorders typically comprise polar solvents which enable the incorporation of the medicaments into the formulation. The major disadvantage of these currently available topical formulations comprising polar solvents, e.g. ethanol, is their stinging effect when applied to the skin or mucosal surface. As used herein, the term "body surface" refers to a skin surface, nails, and mucous membranes (a mucosal surface).

In contrast to currently available topical formulations, the topical compositions of the present invention comprise an aqueous phase which allows dissolution and substantially homogeneous distribution of the pharmaceutical agents. In an embodiment, addition of water to the topical composition reduces the use of stinging polar solvents and hence improves the compliancy of the subject to be treated. It is further disclosed that the topical compositions of the present invention, upon drying, form a film on the body surface and thus provide a protective coating.

In addition, the topical compositions of the present invention, when dried, form a durable film which does not crack or flake off and remains intact for more than 12 hours giving release of the pharmaceutical agent for an extended period of time, thus leading to enhanced healing of the affected areas.

The sustained or extended release of the pharmaceutical agent(s) from the compositions of the present invention enables methods of treatment including less frequent administration (such as once daily, once every other day or twice weekly) than existing commercially available products, while achieving similar or better therapeutic results.

Further, the topical compositions of the present invention, when dried, form a flexible film, closely following irregularities of the body surface as well as movement of the body surface.

According to an aspect, the present invention provides a topical composition that includes:

from about 10.0% (w/w) to about 30.0% (w/w) of a silicone film forming ingredient;

from about 1.0% (w/w) to about 5.0% (w/w) of at least one surfactant selected from the group consisting of sodium lauryl sulfate, alkyl- and alkoxy-dimethicone copolyol, polysorbate and a combination thereof;

from about 30.0% (w/w) to about 75.0% (w/w) of a non-polar volatile siloxane solvent; and from about 0.005% (w/w) to about 25.0% (w/w) of a pharmaceutical agent selected from the group consisting of pramoxine, phenylephrine, hydrocortisone, salicylic acid, nitroglycerine, sildenafil, procaine, lidocaine, tetracaine, dibucaine, prilocalne, phenacaine, benzyl alcohol, benzocaine, diperodon, dyclonine, dimethisoquin, epinephrine, tetrahydrozoline hydrochloride, an amphetamine, an antihistamine, methylphenidate, mephedrone, oxymetazoline, pseudoephedrine, psilocybin, ephedrine sulphate imiquimod, podophyllin, podophylotoxin, fluorouracil, sinecatechins, plant extracts, adapalene, benzoyl peroxide, tazarotene, azelaic acid, clindamycin, acyclovir, penciclovir, famciclovir, docosanol, or their salts and combinations thereof wherein the composition is sufficiently designed to dry within 60 seconds after application to a skin surface or a mucosal surface to form a dried composition, and wherein the dried composition forms:

(i) a flexible film, wherein the flexible film closely follows irregularities of the surface as well as movement of the surface, and (ii) a durable film, wherein the durable film does not crack or flake off and remains intact for more than 12 hours giving release of the pharmaceutical agent for an extended period of time.

According to an aspect, the present invention provides a topical composition that includes:

(i) at least one flexible film forming ingredient, (ii) at least one surfactant, (iii) at least one non-polar volatile solvent (iv) at least 15% (w/w) water, and (v) a therapeutically effective concentration of at least one pharmaceutical agent, wherein the composition is sufficiently designed to dry within 60 seconds after application to a mucosal surface of an anorectal region to form a dried composition, wherein the dried composition forms: (i) a flexible film, wherein the flexible film closely follows irregularities of the mucosal surface as well as movement of the mucosal surface, and (ii) a durable film, wherein the durable film does not crack or flake off and remains intact for more than 12 hours giving release of the pharmaceutical agent for an extended period of time.

According to an embodiment, a topical composition of the present invention is in the form of an emulsion. In an embodiment, the emulsion is an oil-in-water emulsion. The emulsion may be in the form of a viscous gel (25000-45000 cP) or a liquid whose viscosity ranges from 1-1.2 cP, close to the viscosity of water. While the gel is applied to the skin or mucosal surface as such, the liquid emulsion is mainly used for the preparation of the wipes.

The topical compositions of the present invention can be administered as a gel, a wipe, a towellete, a water-based solution, a spray or a foam.

According to one embodiment, the at least one film forming ingredient is selected from the silicone resin group consisting of siloxysilicate, silsesquioxane or other silicone polymers. According to one embodiment, the siloxysilicate is trimethylsiloxysilicate. According to an additional embodiment, the silsesquioxane is polymethylsilsesquioxane.

According to some embodiments, the at least one surfactant is an anionic surfactant. The anionic surfactant can be selected from the group consisting of sodium alkyl sulfate, sodium alkyl sulfonate, sodium alkyl aryl sulfonate, sodium stearate, dioctyl sodium sulfosuccinate, sodium cholate, and any combination thereof. According to a certain embodiment, the sodium alkyl sulfate is sodium lauryl sulfate.

According to further embodiments, the at least one surfactant is a nonionic surfactant. The nonionic surfactant can be selected from the group consisting of organosilicone surfactants, nonionic organic surfactants and a combination thereof. According to some embodiments, the organosilicone surfactant comprises alkyl- and alkoxy-dimethicone copolyol. According to further embodiments, the alkyl- and alkoxy-dimethicone copolyol is cetyl dimethicone copolyol. According to a certain embodiment, the cetyl dimethicone copolyol is Cetyl PEG/PPG-10/1 Dimethicone.

According to further embodiments, the nonionic organic surfactant is selected from the group consisting of polysorbate, glyceryl stearate, polyoxyethylene (POE) fatty acid ester, poly(oxyethylene) alkylyl ether, polyethoxylene castor oil derivative, PEG-6 octanoic/decanoic glycerides, polyoxyethylene glycerol trioleate, decaglycerol mono/dioleate, and any combination thereof. The polysorbate can be selected from the group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80).

According to still further embodiments, the at least one surfactant is a cationic surfactant, an amphoteric surfactant, or a combination thereof.

According to additional embodiments, the volatile solvent is a non-polar volatile siloxane, such as methylsiloxane or a polydimethylsiloxane. According to some embodiments, the volatile polydimethylsiloxane is a linear polydimethylsiloxane or a cyclic polydimethylsiloxane. According to further embodiments, the volatile polydimethylsiloxane is selected from the group consisting of hexamethyldisiloxane, heptamethyloctyltrisiloxane octamethylcyclotetrasiloxane, octamethyltrisiloxane, decamethylcyclopentasiloxane, decamethyltetrasiloxane, dodecamethylpentasiloxane, dodecamethylcyclohexasiloxane, and a combination thereof. According to a certain embodiment, the volatile polydimethylsiloxane is hexamethyldisiloxane.

According to further embodiments, the volatile solvent is a volatile aliphatic hydrocarbon selected from the group consisting of alkanes, alkenes, alkynes, and mixtures thereof. According to yet further embodiments, the alkane is selected from the group consisting of pentane, isooctane, isododecane, isohexadecane and a combination thereof. According to a certain embodiment, the volatile aliphatic hydrocarbon is isooctane. According to another embodiment, the volatile solvent is a combination of a siloxane and isooctane.

According to additional embodiments, the pharmaceutical agent is selected from the group consisting of anesthetic agents, vasoconstrictors, an immunomodulator, a cytotoxin, antipruritic agents, immunomodulators, cytotoxins, anti-inflammatory agents, muscle relaxants, and a combination thereof. Each possibility is a separate embodiment of the invention.

The anesthetic agent can be selected from the group consisting of pramoxine, procaine, lidocaine, tetracaine, dibucaine, prilocalne, phenacaine, benzyl alcohol, benzocaine, diperodon, dyclonine, dimethisoquin, salts thereof, and a combination thereof. According to a certain embodiment, the anesthetic agent is pramoxine. According to some embodiments, the anesthetic agent is present in the topical composition in an amount ranging from about 0.15% (w/w) to about 25% (w/w).

According to further embodiments, the vasoconstrictor is selected from the group consisting of phenylephrine, phenylephrine hydrochloride, epinephrine, epinephrine hydrochloride, tetrahydrozoline hydrochloride an amphetamine, an antihistamine, methylphenidate, mephedrone, oxymetazoline, pseudoephedrine, psilocybin, ephedrine sulphate, and a combination thereof. According to an exemplary embodiment, the vasoconstrictor is phenylephrine. According to some embodiments, the vasoconstrictor is present in the topical composition in an amount ranging from about 0.005% (w/w) to about 2.0% (w/w).

According to a certain embodiment, the pharmaceutical topical composition comprises a combination of pramoxine and phenylephrine.

According to further embodiments, the antipruritic agent is selected from the group comprising corticosteroid, camphor, juniper tar, menthol and a combination thereof. According to a certain embodiment, the corticosteroid is hydrocortisone. According to some embodiments, the antipruritic agent is present in the topical composition in an amount ranging from about 0.1% (w/w) to about 5% (w/w).

According to yet further embodiments, the muscle relaxant is nifedipine, diltiazem verapamil, nitroglycerin, sildenafil, or a salt thereof. According to a certain embodiment, the muscle relaxant is sildenafil citrate. According to some embodiments, the muscle relaxant is present in the topical composition in an amount ranging from about 0.1% (w/w) to about 15% (w/w).

According to still further embodiments, the anti-inflammatory agent is selected from the group consisting of salicylic acid, indomethacin, sodium indomethacin trihydrate, salicylamide, naproxen, colchicine, fenoprofen, sulindac, diflunisal, diclofenac, indoprofen and sodium salicylamide. According to still further embodiment, the anti-inflammatory agent is salicylic acid.

According to some embodiments, a topical composition of the present invention can further comprise an astringent, a keratolytic agent, an antibiotic agent, an antiseptic agent, an antioxidant, a keratolytic, a protectant, an astringent or a combination thereof. Each possibility is a separate embodiment of the invention.

According to some embodiments, a pharmaceutical topical composition of the present invention can further comprise an additive/excipient selected from the group consisting of a dimethicone/vinyl dimethicone crosspolymer, a silicone gum blend, a gelling agent and a combination thereof. Each possibility is a separate embodiment of the invention.

According to a certain embodiment, the dimethicone/vinyl dimethicone crosspolymer comprises bis-vinyldimethicone, vinyldimethicone and hydrogen dimethicone.

According to additional embodiments, the silicone gum blend comprises a blend of high and low molecular weight silicones. According to a certain embodiment, the silicone gum blend comprises cyclopentasiloxane and dimethiconol.

According to additional embodiments, the gelling agent is a cellulose derivative. According to a certain embodiment, the cellulose derivative is hydroxypropyl methyl cellulose. According to other embodiments, the gelling agent is selected from the group consisting of carbomer, carbomer copolymers, gelatin, aluminum monostearat, dextrin, sodium alginate, alginic acid, pectin, acacia, alginic acid, carrageenan, xanthan, tragacanth, magnesium aluminum silicate, bentonite, poloxamers, polyvinyl alcohol, and a combination thereof.

According to some embodiments, a topical composition comprises: (i) trimethylsiloxysilicate; (ii) a surfactant selected from the group consisting of an anionic surfactant, a nonionic surfactant and a combination thereof; (iii) a volatile solvent selected from the group consisting of a siloxane such as methylsiloxane or a polydimethylsiloxane, an aliphatic hydrocarbon, and a combination thereof; (iv) water; and (v) at least one pharmaceutical agent selected from the group consisting of an anesthetic agent, a vasoconstrictor, an antipruritic agent, an immunomodulator, a cytotoxin, an anti-acne agent, an anti-inflammatory agent, a muscle relaxant, and a combination thereof. According to a certain embodiment, the surfactant is an anionic surfactant. According to some embodiments, the topical composition further comprises an additive selected from the group consisting of a dimethicone/vinyl dimethicone crosspolymer, a silicone gum blend, a gelling agent and a combination thereof.

According to some embodiments, a topical composition comprises: (i) about 10% (w/w) to about 40% (w/w) of trimethylsiloxysilicate; (ii) about 0.5% (w/w) to about 7.0% (w/w) of a surfactant selected from the group consisting of sodium lauryl sulfate, alkyl- and alkoxy- dimethicone copolyol, polysorbate, and a combination thereof; (iii) about 30% (w/w) to about 80% (w/w) of a volatile solvent, selected from the group consisting of a siloxane such as methylsiloxane or a polydimethylsiloxane, volatile aliphatic hydrocarbon and a combination thereof; (iv) about 20% (w/w) to about 40% (w/w) of water; and (v) about 0.005% (w/w) to about 25% (w/w) of at least one pharmaceutical agent, selected from the group consisting of pramoxine, phenylephrine, hydrocortisone, acid, nitroglycerine, sildenafil citrate, and a combination thereof. According to a certain embodiment, the at least one surfactant is sodium lauryl sulfate. According to another embodiment, the surfactant is a combination of sodium lauryl sulfate and cetyl dimethicone copolyol. According to additional embodiments, the surfactant is a combination of polysorbate and cetyl dimethicone copolyol. According to some embodiments, cetyl dimethicone copolyol is Cetyl PEG/PPG-10/1 Dimethicone. According to some embodiments, polydimethylsiloxane is hexamethyldisiloxane. According to additional embodiments, volatile aliphatic hydrocarbon is isooctane. According to some embodiments, the topical composition further comprises about 0.2% (w/w) to about 15% (w/w) of an additive selected from the group consisting of bis-vinyldimethicone, vinyldimethicone and hydrogen dimethicone; cyclopentasiloxane and dimethiconol; hydroxypropyl methyl cellulose; and a combination thereof. According to some embodiments, bis-vinyldimethicone, vinyldimethicone and hydrogen dimethicone can be present in the topical composition in an amount ranging from about 5.0% (w/w) to about 15% (w/w). According to further embodiments, cyclopentasiloxane and dimethiconol can be present in the topical composition in an amount ranging from about 0.5% (w/w) to about 2.5% (w/w). According to still further embodiments, hydroxypropyl methyl cellulose can be present in the topical composition in an amount ranging from about 0.05% (w/w) to about 5% (w/w).

According to some embodiments, a topical composition comprises: (i) about 20% (w/w) trimethylsiloxysilicate; (ii) about 3% (w/w) sodium lauryl sulfate; (iii) about 26% (w/w) hexamethyldisiloxane and 20% (w/w) isooctane; (iv) about 30% (w/w) water; and (v) about 1% (w/w) pramoxine as the pharmaceutical agent. Alternatively, the pharmaceutical agent is phenylephrine in an amount of about 0.05% (w/w). Further alternatively, the pharmaceutical agent is a combination of about 1% (w/w) pramoxine and about 0.25% (w/w) phenylephrine. Still further alternatively, the pharmaceutical agent is hydrocortisone in an amount of about 1% (w/w), or salicylic acid in an amount of about 1.0% (w/w) to about 20% (w/w), or nitroglycerine in an amount of about 0.2% (w/w) to about 0.5% (w/w), or sildenafil citrate in an amount of about 10% (w/w), or nifedipine in an amount of about 0.1% (w/w) to about 5% (w/w) diltiazem in an amount of about 0.1% (w/w) to about 5.0% (w/w), or verapamil in an amount of about 0.1% (w/w) to about 5% (w/w) or a combination thereof.

According to a certain embodiment, a topical composition comprises: (i) about 20% (w/w) trimethylsiloxysilicate; (ii) about 3% (w/w) sodium lauryl sulfate; (iii) about 26% (w/w) hexamethyldisiloxane and 20% (w/w) isooctane; (iv) about 30% (w/w) water; (v) about 1% (w/w) pramoxine; and (vi) about 0.05% (w/w) phenylephrine.

According to further embodiments, a topical composition comprises: (i) about 20% (w/w) trimethylsiloxysilicate; (ii) about 1.5% (w/w) sodium lauryl sulfate; (iii) about 4% (w/w) Cetyl PEG/PPG-10/1 Dimethicone (iv) about 24% (w/w) hexamethyldisiloxane and 20% (w/w) isooctane; (v) about 30% (w/w) water; and (vi) about 1% (w/w) pramoxine as the pharmaceutical agent. Alternatively, the pharmaceutical agent is phenylephrine in an amount of about 0.25% (w/w). Further alternatively, the pharmaceutical agent is a combination of about 1% (w/w) pramoxine and about 0.25% (w/w) phenylephrine. Still further alternatively, the pharmaceutical agent is hydrocortisone in an amount of about 1% (w/w), yet further alternatively the pharmaceutical agent is imiquimod in an amount of about 4% (w/w) to about 5.0% (w/w), or podophyllotoxin in an amount of about 0.5% (w/w), or 5-fluorouracil in an amount of about 0.1% (w/w) to about 10% (w/w), or salicylic acid in an amount of about 1.0% (w/w) to about 20% (w/w), or nitroglycerine in an amount of about 0.2% (w/w) to about 0.5% (w/w), or sildenafil citrate in an amount of about 10% (w/w), or nifedipine in an amount of about 0.1% (w/w) to about 5.0% (w/w) diltiazem in an amount of about 0.1% (w/w) to about 5.0% (w/w), or verapamil in an amount of about 0.1% (w/w) to about 5.0% (w/w) or a combination thereof.

According to still further embodiments, a topical composition comprises: (i) about 20% (w/w) trimethylsiloxysilicate; (ii) about 1.5% (w/w) Tween 80; (iii) about 4% (w/w) Cetyl PEG/PPG-10/1 Dimethicone (iv) about 24% (w/w) hexamethyldisiloxane and 20% (w/w) isooctane; (v) about 30% (w/w) water; and (vi) about 1% (w/w) pramoxine as the pharmaceutical agent. Alternatively, the pharmaceutical agent is phenylephrine in an amount of about 0.25% (w/w). Further alternatively, the pharmaceutical agent is a combination of about 1% (w/w) pramoxine and about 0.25% (w/w) phenylephrine. Still further alternatively, the pharmaceutical agent is hydrocortisone in an amount of about 1% (w/w), or salicylic acid in an amount of about 1.0% (w/w) to about 20% (w/w), or nitroglycerine in an amount of about 0.2% (w/w) to about 0.5% (w/w), or sildenafil citrate in an amount of about 10% (w/w), or nifedipine in an amount of about 0.1% (w/w) to about 5.0% (w/w) diltiazem in an amount of about 0.1% (w/w) to about 5.0% (w/w), or verapamil in an amount of about 0.1% (w/w) to about 5.0% (w/w) or a combination thereof.

According to some embodiments, the pH of a topical composition of the present invention is from about 3.5 to about 5. According to other embodiments, the pH of a topical composition of the present invention is from about 4.0 to about 4.6. According to additional embodiments, the pH of a topical composition of the present invention is from about 4.2 to about 4.4. According to some embodiments, the pH is maintained using citrate buffer.

According to another aspect, the present invention provides a method of treating or preventing a topical disorder, the method comprising the step of topically applying to a body surface of a subject in need of such treatment a therapeutically effective amount of a topical composition of the present invention.

According to some embodiments, the topical disorder is selected from the group consisting of hemorrhoids, anal fissures, anal cracks, anal fistulas, anal abscesses and anal pruritus dermatitis, acne, rosacea, onychomycosis, pityriasis, actinic keratosis, eczema, erythema, urticaria, common warts, genital warts, anal warts, herpes and many others.

According to a certain embodiment, the topical disorder is an anorectal disorder selected from one of hemorrhoids, fissure or anal pruritus.

According to a certain embodiment, the topical disorder is genital or anal warts and herpes.

According to a certain embodiment, the topical disorder is acne or rosacea.

According to additional embodiments, if the anorectal disorder is hemorrhoids, the pharmaceutical agent is an anesthetic agent, a vasoconstrictor, or a combination thereof. According to a certain embodiment, the topical composition for use in treating or preventing hemorrhoids comprises a combination of about 1% (w/w) pramoxine and about 0.25% (w/w) phenylephrine.

According to some embodiments, if the anorectal disorder is anal pruritus, the topical composition for use in treating or preventing anal pruritus comprises an antipruritic agent. According to a certain embodiment, the antipruritic agent is hydrocortisone in an amount of about 1% (w/w) hydrocortisone.

According to some embodiments, if the anorectal disorder is anal fissures, the pharmaceutical agent to be administered is a muscle relaxant. According to an exemplary embodiment, the topical composition comprises about 0.1% (w/w) to about 0.5% (w/w) nifedipine, diltiazem in an amount of about 0.1-5% w/w, or verapamil in an amount of about 0.1% (w/w) to about 5.0% (w/w) or about 0.2% (w/w) to about 0.5% (w/w) nitroglycerine, or about 10% (w/w) sildenafil citrate.

According to one embodiment, the subject to be treated is a human being. According to another embodiment, the subject to be treated is an animal.

According to yet another aspect, the present invention provides a kit comprising a topical composition of the present invention, a container-applicator device suitable for storage and application of the composition to a body surface, and instructions for administering the topical composition to a subject in need thereof.

According to some embodiments, the container-applicator device is selected from the group consisting of a single use wipe, a syringe, a dropper, a spray dispenser, a swab, a compressible bottle or tube, a spatula, a suppository insertion tube, an extrusion tube, a pump dispenser, a pressurized dispenser and an inflatable member.

According to another aspect, the present invention provides a topical composition for use in treating or preventing an anorectal disorder.

Other objects, features and advantages of the present invention will become clear from the following description and claims.

A topical composition of the present invention comprises at least one film forming agent, at least one surfactant, at least one non-polar volatile solvent, water and at least one pharmaceutically active agent. One such film forming agent may be a silicone resin. The topical composition can further comprise additives, such as dimethicone/vinyl dimethicone crosspolymers, silicone gum blends and gelling agents.

The term "film forming agent" or "film forming ingredient" or "film former", as used herein, means an inactive ingredient such as a silicone resin that after dissolution in at least one solvent and application on a substrate leaves a film on the substrate to which it is applied, for example once the at least one solvent evaporates, absorbs and/or dissipates on the substrate.

The anorectal disorders have a unique feature which is only shared with topical use on skin and joints. Anal fissure (a tear in the anus) and hemorrhoids both extend significantly during defecation, which causes reopening of the anal fissure, bleeding, itching and pain. Therefore, flexible films possess a distinct advantage for the treatment of anorectal disorders such as anal fissure and hemorrhoids, providing a better protection of the wound, and reduction of bleeding, itching and pain during extension that occurs during defecation.

Silicone resins, such as polydimethylsiloxane and polymethylsilsesquioxane have an unique semi-organic structure and are flexible.

While using film forming agents in the instant invention, it is desirable to use such flexible film forming agents and formulate them in such compositions which produce flexible and durable films. In an embodiment, there are provided flexible and durable film forming compositions, providing beneficial therapeutic effects like reduced bleeding, pain and itching.

The durability and flexibility of the films formed from the compositions of the present invention on drying were investigated by applying the composition L of Table 2, Example 3 on the elbow, neck and internal part of the arm of a patient. Shortly thereafter (about 20 seconds) the composition dried and left a thin film on the skin. The films were examined after 12, 18 and 24 hrs for durability and flexibility. During this period the patient carried out their usual daily activities and took one shower.

It was found that the films remained intact after 12, 18 and 24 hrs. The films did not fall off the body surface and did not crack or flake off. It was found that the films remained flexible after 12, 18 and 24 hrs. The films closely followed the patient's skin irregularities as well as skin movement throughout the day during normal activity. The skin under the film was slightly pale, which shows the vasoconstrictor phenylephrine was still active after 24 hrs. After 24 hrs, the film was removed from the skin and tested by high performance liquid chromatography (HPLC), whereupon significant amounts of the two actives (pramoxine and phenylephrine) were found in the film despite the extended period of time.

The film formed on the skin or mucosal surface allows the tissues to "breathe", which is beneficial because of the extended period of time the film stays on the tissues.

The compositions of the instant invention dry relatively fast after application on the skin or mucossal surface between 5 seconds and 1 minute to form a durable and elastic film.

The film formed on the substrate is substantially dry, which means it contains less than 10% volatiles. In an embodiment, the dried film formed on the substrate contains less than 5% volatiles. In an embodiment, the dried film formed on the substrate contains less than 2% volatiles. The important aspect of the substantially dry films of this invention, whatever the percentage of volatiles left, is that they feel dry to touch and do not soil, stain or otherwise absorb into the underwear.

Most of the commercially available topical formulations are in the form of cream, ointment, enema, suppositories or other forms of administration which leave on the anus and rectum a greasy deposit which is very problematic, because of the potential of staining, soiling or otherwise absorbing into the underwear.

In an embodiment, there are provided non-soiling compositions, affording convenience for the patient, improving patient compliance and avoiding embarrassment.

Commercially available anorectal products and compositions are usually applied several times daily and before each defecation.

Thus, for example, Preparation H® Maximum Strength, containing phenylephrine HCl 0.25% and Pramoxine HCl 1% is applied "up to 4 times daily, especially at night, in the morning or after each bowel movement".

It has been surprisingly found that compositions of the instant invention may be administered less often than commercial products containing the same pharmaceutically active agents in the same concentrations.

Thus, in a comparative clinical study, composition PP-110 (see Example 8) of the instant invention containing HCl 0.25% (w/w) and Pramoxine HCl 1% (w/w) (the same pharmaceutical actives in the same concentrations as Preparation H®) showed comparable or superior results compared to the Preparation-H arm in one or both of PP-110 arms. This includes pain, itching, swelling, bleeding and discomfort, and was achieved even though PP-110 was applied once daily and Preparation-H was applied 4 times per day. It is believed that, as a result, the patient is exposed to a much lower dose of the active pharmaceutical ingredient(s).

Without wishing to be bound by theory, the inclusion of the active pharmaceutical in the flexible film seems to have a long-acting or sustained release effect, achieving comparable or superior results compared to similar commercial products, while exposing the patient to smaller amounts of the active pharmaceutical ingredient(s).

In an embodiment, there are provided anorectal compositions achieving a similar or better therapeutic effect than a commercially available composition comprising the same active pharmaceutical agent(s) in the same concentrations wherein applied several times daily.

In an embodiment, there are provided once daily anorectal topical compositions comprising:
  (i) at least one flexible film forming ingredient;
  (ii) at least one surfactant;
  (iii) at least one non-polar volatile solvent;
  (iv) at least 15% w/w water; and
  (v) a therapeutically effective concentration of at least one pharmaceutical agent,
  wherein the composition is sufficiently designed to dry within 60 seconds after application to a mucosal surface of an anorectal region to form a dried composition, wherein the dried composition forms: (i) a flexible film, wherein the flexible film closely follows irregularities of the mucosal surface as well as movement of the mucosal surface, and (ii) a durable film, wherein the durable film does not crack or flake off and remains intact for more than 12 hours giving release of the pharmaceutical agent for an extended period of time. The dried film in non-soiling. The above compositions may be topically administered even less often than once daily, such as once every other day or twice weekly.

In an embodiment, there are provided once daily anorectal topical compositions comprising:
(i) at least one flexible film forming ingredient;
(ii) at least one surfactant;
(iii) at least one non-polar volatile solvent;
(iv) at least 15% w/w water;
(v) at least one viscosity modifier; and
(vi) a therapeutically effective concentration of at least one pharmaceutical agent,
wherein the composition is sufficiently designed to dry within 60 seconds after application to a mucosal surface of an anorectal region to form a dried composition, wherein the dried composition forms: (i) a flexible film, wherein the flexible film closely follows irregularities of the mucosal surface as well as movement of the mucosal surface, and (ii) a durable film, wherein the durable film does not crack or flake off and remains intact for more than 12 hours giving release of the pharmaceutical agent for an extended period of time. The dried film in non-soiling.

In an embodiment there is provided a method of treatment of anorectal compositions, the method comprising the step of topically applying once daily, or once every other day or twice weekly to the mucosal surface of an anorectal region of a subject in need of such treatment, a therapeutically effective concentration of a topical composition of the present invention.

The selection of the inactive pharmaceutical ingredients and their concentration has an impact on the therapeutic effect of the compositions, so that extensive experimentation was needed until the optimal compositions were developed. Thus, for example, low concentrations of water result in incomplete solubilization of the active(s) and high water concentrations lead to slow rate of drying.

It has been surprisingly found that when a topical composition of the present invention is formulated for use as a wipe, the addition of inactive ingredients like Pemulen®, have a profound effect on the viscosity of the compositions, lowering the viscosity even at concentrations below 0.1% w/w. Therefore, Pemulen® may be included in the composition for the wipes, which requires a lower viscosity.

In an embodiment, the film forming agents used in the compositions of the present invention are non-polymerizable and therefore, unlike the polymerizable agents are less sensitive to moisture, more stable and more suitable for repeated use.

The term "volatile solvent", as used herein, means that the solvent has a measurable vapor pressure. Suitable volatile solvents used in this invention are non-polar solvents.

Some of the film forming agents according to the present invention are silicone resins. The non-limiting examples of silicone resins useful in the compositions of the invention are siloxysilicates, silsesquioxanes (usually denoted as T-resins) and a combination thereof. One non-limiting example of a siloxysilicate in accordance with the present invention is trimethylsiloxysilicate, which may be represented by the following formula:

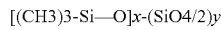

[(CH3)3-Si—O]x-(SiO4/2)y wherein x and y may, for example, range from 50 to 80. Such siloxysilicates are commercially available from General Electric and Dow Corning under the trade name Resin MQ®. One non-limiting example of silsesquioxane is polymethylsilsesquioxane. Trimethylsiloxysilicate and polymethylsilsesquioxane are widely used in cosmetic industry due to their film forming properties, as described, for example, in U.S. Pat. Nos. 7,879,316 and 7,879,346 and U.S. Patent Application Publication No. 2005/0201961. The present invention discloses for the first time the use of trimethylsiloxysilicate for therapeutic applications, inter alia, for treatment of anorectal disorders. Trimethylsiloxysilicate is soluble in the volatile solvent of a topical composition of the present invention. The amount of the silicone resin film forming agent in the composition is determined based on the desired adhesion properties of the dried film to the target surface. The amount depends, inter alia, on the target surface, the condition to be treated, and the amount of composition ingredients. The amount of the silicone resin film forming agent further defines the viscosity of the topical composition. The amount of the silicone resin film forming agent in the composition typically ranges from about 10% (w/w) to 40% (w/w). The term "about" as used herein denotes ±10% of the value indicated.

In an embodiment, the volatile solvent useful for dissolving the silicone resin is chosen from volatile silicone or volatile aliphatic hydrocarbon. In an embodiment, water solubility of the volatile solvent is less than about 0.1% (w/w). According to some embodiments, the volatile silicone solvent is a linear or cyclic polydimethylsiloxane, having from 2 to 9 silicon atoms, these silicones being optionally substituted with alkyl or alkoxy groups of 1 to 10 carbon atoms. The non-limiting examples of a siloxane such as methylsiloxane or a polydimethylsiloxanes in accordance with the present invention are hexamethyldisiloxane, heptamethyloctyltrisiloxane octamethylcyclotetrasiloxane, octamethyltrisiloxane, decamethylcyclopentasiloxane, decamethyltetrasiloxane, dodecamethylpentasiloxane, dodecamethylcyclohexasiloxane, and mixtures thereof. A suitable polydimethylsiloxane used in the compositions is hexamethyldisiloxane.

The volatile solvent can further comprise a volatile aliphatic hydrocarbon. The aliphatic hydrocarbon in accordance with the present invention may be any aliphatic hydrocarbon, including an alkane, a mixture of alkanes, an alkene, a mixture of alkenes, an alkyne, a mixture of alkynes, an ester or a mixture thereof. A suitable aliphatic hydrocarbon is an alkane such as pentane, isooctane, isododecane, isohexadecane or a mixture thereof. According to a certain embodiment, the aliphatic hydrocarbon is isooctane. The volatile ester useful for dissolving the film former may be a branched ester, such as isohexyl or isodecyl neopentanoate and mixture thereof.

The volatile solvent may comprise a volatile silicone, a volatile aliphatic hydrocarbon or a mixture thereof. According to a certain embodiment, the volatile solvent comprises methylsilozane or a hexamethyldisiloxane and isooctane.

According to some embodiments, the presence of water in a topical composition of the present invention allows dissolution of the pharmaceutically active agents, which are not soluble in the non-polar volatile solvents used for dissolving the film-former, thus avoiding the need to use polar solvents. As the pharmaceutically active agents are completely dissolved in the compositions of the present invention and do not precipitate or crystallize on drying, the resulting essentially dry films comprising the active(s) are clear, transparent and not "white films".

The emulsion can be a water-in-oil or oil-in-water emulsion. According to exemplary embodiments, a topical composition of the present invention is an oil-in-water emulsion, wherein the aqueous phase includes the pharmaceutical agents dissolved therein and the oil phase includes the film forming agent dissolved in the volatile solvent. The oil-inwater emulsion allows the film former and the pharmaceutical active agents to be homogeneously dispersed in the topical composition. The stable emulsion provides fine dispersion of the emulsion ingredients in the topical composition, in the container-applicator device and upon the application to the target surface, such that once the volatile solvent and water evaporate both the film former and the pharmaceutical active ingredients remain finely dispersed on the target surface. The stable emulsion prevents clamping, floating and/or precipitation of the polar active ingredients in the non-polar volatile solvents. The presence of the aqueous phase in the topical composition further obviates the use of polar solvents, formerly required to dissolve and disperse pharmaceutical active ingredients in silicone based liquid bandages.

The amount of the volatile solvent and water affects the viscosity and evaporation time of the topical composition when applied to a target surface. The amount of the volatile solvent and water is determined so as to adjust the viscosity and evaporation time to desired values. The amount of volatile solvent and water further affects the morphology of the silicone/water emulsion. The amount of the volatile solvent can be adjusted to obtain the desired emulsion type. The amount of the volatile solvent in the composition typically ranges from about 30% (w/w) to about 80% (w/w). The amount of water can be adjusted to obtain the desired emulsion type. The amount of water in the composition typically ranges from about 20% (w/w) to about 40% (w/w).

The topical compositions of the present invention further comprise at least one surfactant. Addition of the surfactant allows mixing of the silicone and the aqueous phases, producing a silicone/water emulsion. Addition of the surfactant further allows the emulsion stabilization. As described hereinabove, the obtained emulsion may be an oil-in-water emulsion, wherein the aqueous phase includes dissolved pharmaceutical ingredients and finely dispersed volatile solvent phase, containing the dissolved film former.

The surfactant is selected from the group consisting of an anionic surfactant, a non-ionic surfactant, selected from organosilicone surfactant or nonionic organic surfactant, a cationic surfactant, an amphoteric surfactant and a combination thereof. Each possibility is a separate embodiment of the invention.

The anionic surfactants usable in the compositions of the present invention include sodium alkyl sulfates, such as, but not limited to sodium lauryl sulfate; sodium alkyl sulfonates; sodium alkyl aryl sulfonates, such as sodium dodecyl benzene sulfonate and the like; sodium stearate; dioctyl sodium sulfosuccinate; sodium cholate; and a combination thereof.

Examples of suitable organosisilicone surfactants include, but are not limited to dimethicone copolyols such as; alkoxy dimethicone copolyols, alkyl and alkoxy-dimethicone copolyols, silicones having pendant hydrophilic moieties such as linear silicones having pendant polyether groups, branched polyether and alkyl modified silicones, branched polyglycerin and alkyl modified silicones. A suitable dimethicone copolyol is cetyl dimethicone copolyol, such as Cetyl PEG/PPG-10/1 Dimethicone sold under the name Abil EM-90. Other suitable dimethicone copolyols include branched polyether and alkyl modified silicones such as Lauryl PEG-9 Polydimethylsiloxyethyl Dimethicone sold under the name KF-6038, and branched polyglycerin and alkyl modified silicones such as Lauryl Polyglyceryl-3 Polydimethylsiloxyethyl Dimethicone sold under the name KF-6105. Additional dimethicone copolyols useful in the compositions of the present invention include bis-PEG/PPG-14/dimethicone copolyol sold under the name Abil EM-97 and the polyglyceryl-4 isostearate/cetyl dimethicone copolyol/hexyl laurate mixture sold under the name Abil WE 09. Another suitable dimethicone copolyol is PEG-9 Polydimethylsiloxyethyl Dimethicone sold under the name KF-6028. Abil EM-90, Abil EM-97 and Abil WE 09 are available from Evonik Goldschmidt GmbH of Essen, Germany. KF-6038 are KF-6105 are available from Shin-Etsu Silicones of Akron, Ohio.

Non-limiting examples of possible non-ionic organic surfactants include polysorbates, such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80); glyceryl stearate; polyoxyethylene (POE) fatty acid esters, such as Myrj 45, Myrj 49, Myrj 52 and Myrj 59; poly(oxyethylene) alkylyl ethers, such as poly(oxyethylene) cetyl ether (Brij 52, Brij 56, Brij 58), poly(oxyethylene) palmityl ether, polyethylene oxide hexadecyl ether, polyethylene glycol cetyl ether, and the like; polyethoxylene castor oil derivatives, such as Cremophor EL, ELP and RH 40; PEG-6 octanoic/decanoic glycerides, such as Softigen 767 and the like; polyoxyethylene glycerol trioleate, such as but not limited to Tagat TO; decaglycerol mono/dioleate, such as Caprol PGE860 and the like; and a combination thereof.

The nonionic organic surfactants may further comprise sorbitan fatty acid esters, such as sorbitan monolaurate (Span 20), sorbitan monopalmitate (Span 40), sorbitan monooleate (Span 80), sorbitan monostearate (Span 60); mono/diglycerides of octanoic/dectanoic acids, such as but not limited to Imwitor-742, Imwitor-308, and a combination thereof.

Non-limiting examples of possible cationic surfactants include phosphatides, such as phosphatidyl choline and the like; quaternary ammonium cationic surfactants, such as hexadecyltrimethyl ammonium bromide and the like; pyrimidinium cationic surfactants, such as, but not limited to dodecyl pyridinium chloride; and a combination thereof.

The amphoteric surfactant may include lecithine, N-dodecyl alanine, cocamidopropyl amino betaine or a combination thereof.

The type and the amount of surfactant may be determined by a person skilled in art so as to obtain the Hydrophile-Liphophile Balance (HLB) of the surfactant or the surfactant mixture suitable for the oil-in-water systems.

According to some embodiments, the surfactant used in the compositions of the present invention is an anionic surfactant. According to additional embodiments, the surfactant may further comprise nonionic surfactant. The nonionic surfactant may be selected from the group consisting of nonionic organic surfactant, organosilicone surfactant and a combination thereof. According to other embodiments, the surfactant in the compositions of the present invention is a nonionic surfactant.

According to an embodiment, the surfactant is sodium alkyl sulfate, such as sodium lauryl sulfate. According to other embodiments, the surfactant is a combination of sodium alkyl sulfate and alkyl and alkoxy-dimethicone copolyol, for example, sodium lauryl sulfate and Cetyl PEG/PPG-10/1 Dimethicone. According to other embodiments, the surfactant is selected from polyoxyethylene sorbitan monolaurate (Tween 20), polyoxyethylene sorbitan monopalmitate (Tween 40), polyoxyethylene sorbitan monostearate (Tween 60), polyoxyethylene sorbitan monooleate (Tween 80) or any mixture thereof. According to further embodiments, the silicone surfactant is a combination of polysorbate alkyl and alkoxy- dimethicone copolyol, for example, polyoxyethylene sorbitan monooleate (Tween 80) and Cetyl PEG/PPG-10/1 Dimethicone.

A topical composition of the present invention may further comprise an additive selected from the group consisting of dimethicone/vinyldimethicone crosspolymers, silicone gum blends, gelling agents, and a combination thereof.

The dimethicone/vinyldimethicone crosspolymer is available, for example, from Dow Corning as Dow Corning 9506 Cosmetic Powder. According to other embodiments, the dimethicone/vinyldimethicone crosspolymer can be present in the compositions of the present invention in a form of two-part silicone elastomer. Without being bound to any mechanism of action, the addition of two-part silicone elastomers to the topical composition can provide enhanced film adhesion onto the target surface and can allow reduction of skin strain, which may be caused by the silicone resin. The two-part silicone elastomers form a crosspolymer network by addition reaction, upon mixing the two parts, enhancing the composition adhesive properties. One part of the two-part silicone elastomer usually contains vinyl end-blocked silicone polymer and a catalyst suitable for promoting the addition reaction and another part contains vinyl endblocked silicone polymer and silicone polymer carrying SiH groups. These two parts are stored separately before use and the crosslinking reaction starts upon mixing the two parts in a defined ratio. The ratio of the two parts is usually 50:50 and the crosslinking reaction may proceed at room temperature (25±5° C.). The two-part silicone elastomers may comprise dimethicone, hydrogen dimethicone, vinyldimethicone, bis-vinyldimethicon and phenyltrimethicone. According to a certain embodiment, the topical composition of the present invention comprises bis-vinyldimethicone as the first part of the two-part silicone elastomers and vinyldimethicone and hydrogen dimethicone as the second part. The first part can further contain a platinum catalyst. The bis-vinyldimethicone, vinyldimethicone and hydrogen dimethicone are available, for example, from KCC as SM9010™ or SM9020™. The amount of the dimethicone/vinyldimethicone in the composition may be in a range from about 5.0% (w/w) to about 15% (w/w).

The topical compositions of the present invention may further comprise a silicone gum blend. Without being bound to any mechanism of action, the addition of the silicone gum blend provides enhancement of silkiness of the film. Silicone gum blend may be a blend of a high molecular weight and a low molecular weight silicone. In an embodiment, the average molecular weight of the high molecular weight silicone is 100,000 or greater. In an embodiment, the average molecular weight of the low molecular weight silicone is 10,000 or less. High molecular and low molecular weight silicones may comprise dimethicone and/or dimethiconol. The non-limiting examples of a silicone gum blend are cyclopentasiloxane and dimethiconol, and cyclotetrasiloxane and cyclopentasiloxane and dimethiconol. The cyclopentasiloxane and dimethiconol blends are available, for example, from KCC as SF9902E™ or from Momentive as Silsoft 1215 dimethicone™ The amount of the silicone gum blend in the composition may be in a range from about 0.5% (w/w) to about 2.5% (w/w).

The gelling agent increases the aqueous phase viscosity when introduced in said aqueous phase. Without being bound to any mechanism of action, the topical composition in form of a gel comprises pharmaceutical agents primordially dissolved in the aqueous phase of the emulsion, finely dispersed in the continuous jelly phase and the silicone resin, primordially dissolved in the volatile solvent and finely dispersed in the aqueous phase of the emulsion, dispersed in the continuous jelly phase of the topical composition.

The gelling agent useful in a topical composition of the present invention may comprise hydroxypropyl cellulose, hydroxyethyl cellulose, hydroxypropyl methyl cellulose, methyl cellulose, ethyl cellulose, carboxymethyl cellulose, carbomer, carbomer copolymers, gelatin, aluminum monostearat, dextrin, sodium alginate, alginic acid, pectin, acacia, alginic acid, carrageenan, xanthan, tragacanth, magnesium aluminum silicate (Veegum®), bentonite, poloxamers (Pluronics®), polyvinyl alcohol, or mixtures thereof. Each possibility is a separate embodiment of the invention. Suitable gelling agents are cellulose derivatives. According to one embodiment, the gelling agent is hydropropyl methylcellulose. According to some embodiments, the gelling agent is not soluble is the volatile solvent and/or in the silicone oil phase of the emulsion. The amount of the gelling agent in the composition may be in a range from about 0.05% (w/w) to about 5.0% (w/w).

According to some embodiments, the pH is maintained in the range from about 3.5 to about 5, or from about 4.0 to about 4.6, or from about 4.2 to about 4.4 using an appropriate buffering system. The non-limiting examples of the weak acids suitable for buffering the compositions of the present invention include citric acid, citric acid monohydrate, boric acid, and phosphoric acid. Examples of some acid salts which can be used in the buffering systems of the compositions of the present invention include, but are not limited to, sodium citrate, sodium citrate dihydrate, monopotassium phosphate, and disodium phosphate.

Upon application of a topical composition to a body or mucosal surface, the volatile solvent and water evaporate, leaving an adhered, dry film which includes at least one pharmaceutically active agent. The dried film is elastic and durable. It is to be appreciated that the compositions of the present invention are devoid of polar solvents required for dissolving active ingredients, thus providing non-stinging topical compositions that have a comfortable feel when applying on the mucosal anal/genital surface.

The emulsions of the instant invention possess the advantage of reduced stinging effect in comparison with non-aqueous or polar compositions.

In an embodiment, the compositions of the instant invention are essentially non-stinging.

In an embodiment, the compositions of the present invention are devoid of acrylates. The adhesiveness of the compositions does not require acrylates.

Pharmaceutical Agents

The compositions of the present invention further comprise at least one pharmaceutically active agent, such as an anesthetic agent, a vasoconstrictor, an antipruritic agent, an anti-inflammatory agent, a muscle relaxant, an astringent, a keratolytic agent, an immunomodulator, a cytotoxin, an antibiotic agent, an antiseptic agent, an anti-acne agent or a combination thereof. Each possibility is a separate embodiment of the invention. Additional pharmaceutical active agents include for example, analgesics, antimicrobial agents and botanical products or extracts. The compositions of the present invention may further comprise antioxidants. The compositions may further contain one or more protectant active ingredients, excipients and carriers. Pharmaceutically and dermatologically acceptable excipients and carriers as are known in the art may be included in the composition, in particular for maintaining the stability and sterility of the composition, and for promoting delivery, release and/or application of the active agent(s) to the body surface to which the composition is applied.

It is to be understood that the compositions may contain more than one active agent, and/or may be suitable for use in treating different anorectal or genital disorders. The pharmaceutically active agent and the dosage thereof is dependent upon the particular condition to be treated, the age of the subject and other factors evident to those skilled in the art. In an exemplified embodiment, the composition comprises an anesthetic agent and a vasoconstrictor. Anesthetic agents include, but are not limited to, pramoxine, procaine, lidocaine, tetracaine, dibucaine, prilocalne, phenacaine, benzyl alcohol, benzocaine, diperodon, dyclonine, dimethisoquin and combinations thereof. Exemplary anesthetic agent is pramoxine. Pharmaceutically acceptable salts of the aforementioned anesthetic agents may also be included in the composition of the invention. Suitable amounts of such anesthetic agents in the composition may be readily ascertained by one of ordinary skill in the art, and may range, for example, between 0.15% and 25% by weight. In a particular embodiment, the anesthetic agent is pramoxine HCl or lidocaine. In a particular embodiment, the composition of the invention comprises pramoxine HCl at a concentration of 1% w/w based on the total weight of the composition.

Vasoconstrictors which are suitable for use in the invention include amphetamines, antihistamines, methylphenidate, mephedrone, oxymetazoline, phenylephrine, pseudoephedrine, psilocybin, phenylephrine hydrochloride, ephedrine sulphate, epinephrine, epinephrine hydrochloride, tetrahydrozoline hydrochloride, and combinations thereof. Suitable amounts of such vasoconstrictor agents in the composition may be readily ascertained by one of ordinary skill in the art, and may range, for example, between about 0.005% (w/w) to about 2.0% (w/w). Exemplary vasoconstrictor agent is phenylephrine HCl. In a particular embodiment, the composition of the invention comprises phenylephrine HCl at a concentration of about 0.25% (w/w) based on the total weight of the composition.

Antipruritic agents which are suitable for use in the invention include corticosteroids, camphor, juniper tar and menthol. The non-limiting examples of corticosteroids include hydrocortisone, fluocinolone, flurandrenolide, triamcinolone, fluticasone, and desonide. Antipruritic agents may further comprise corticosteroids such as tetrahydrocortisol, prednisone; prednisolone, fludrocortisone, 11-desoxycortisol, cortisone, corticosterone, paramethasone, betamethasone, dexamethasone, desoxycorticosterone acetate, desoxycorticosterone pivalate, fludrocortisone acetate, cortisol acetate, cortisol cypionate, cortisol sodium phosphate, cortisol sodium succinate, beclopmethasone dipropionate, betamethasone, betamethasone sodium phosphate and acetate, betamethasone dipropionate, betamethasone valerate, betamethasone benzoate, cortisone acetate, dexamethasone, dexamethasone sodium phosphate, dexamethasone acetate, fuprednisolone, meprednisone, methylprednisolone, methylprednisolone acetate, methylprednisolone sodium succinate, paramethasone acetate, prednisolone, prednisolone acetate, prednisolone sodium phosphate, prednisolone sodium succinate, prednisolone tebutate, prednisone, triamcinolone acetonide, triamcinolone diacetate, triamcinolone hexacotonide, desoximetasone, flumethasone pivalate, fluocinolone acetonide, fluocinonide, fluorometholone, halcinonide, and medrysone. Suitable amounts of antipruritic agents in the composition may be readily ascertained by one of ordinary skill in the art, and may range, for example, between about 0.1% (w/w) to about 5.0% (w/w).

Anti-inflammatory agents include salicylic acid, indomethacin, sodium indomethacin trihydrate, salicylamide, naproxen, colchicine, fenoprofen, sulindac, diflunisal, diclofenac, indoprofen and sodium salicylamide.

Muscle relaxants which are suitable for use in the invention include nitroglycerin, nifedipine, diltiazem, verapamil, amlodopine, sildenafil, tizanidine, and baclofen, or salts thereof including, but not limited to, sildenafil citrate. Suitable amounts of such muscle relaxants in the composition may be readily ascertained by one of ordinary skill in the art, and may range, for example, between about 0.1% (w/w) to about 15.0% (w/w).

Anti-acne agents are selected from the group comprising adapalene, benzoyl peroxide, tazarotene, azelaic acid, and clindamycin.

A topical composition of the present invention may further include an astringent. As used herein, an "astringent" refers to a substance that causes tissue (e.g., a hemorrhoidal) to contract and can optionally arrest secretion or control bleeding from tissue. Astringents which are suitable for use in the invention include, e.g., alum, tannic acid, calamine, witch hazel, zinc oxide, or a combination thereof. Suitable amounts of such astringents in the composition may be readily ascertained by one of ordinary skill in the art, and may range, for example, between about 2.0% (w/w) to about 50% (w/w).

A topical composition of the present invention may further include a keratolytic agent. As used herein, a "keratolytic agent" refers to a substance that causes desquamation (loosening) and debridement or sloughing of the surface cells of the epidermis. Typically, the keratolytic agent used in the compositions of the present invention is pharmaceutically acceptable for topical use in humans. Suitable keratolytic agents include, but are not limited to, alcloxa, resorcinol, or a combination thereof. Suitable amounts of such keratolytic agents in the composition may be readily ascertained by one of ordinary skill in the art, and may range, for example, between about 0.1% (w/w) to about 5.0% (w/w).

Antibiotics for use in the invention are typically those suitable for topical application. The antibiotic(s) may be classified in one or more of the following groups: penicillins, cephalosporins, carbepenems, beta-lactam antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, and echinocandins.

Specific examples of antibiotics which are suitable for use in the invention include: amikacin, aminosidine, paromomycin, chloramphenicol, ciprofloxacin, clindamycin, colistimethate-sodium, colistin, enfuvirtid, enoxacin, erythromycin, flucloxacillin, fosfomycin, fusafungin, gentamicin, levofloxacin, linezolid, mefloquin, metronidazol, mezlocillin, moxifloxacin, mupirocin, norfloxacin, ofloxacin, oxacillin, penicillin G, penicillin V, phenoxymethylpenicillin, phenoxymethylpenicillin-benzathin, pipemidinic acid, piperacillin, piperacillin+tazobactam, proguanil, propicillin, pyrimethamine, retapamulin, rifaximin, roxithromycin, sodium sulfacetamide, sulbactam, sulbactam+ampicillin, sulfadiazine, spiramycin, sultamicillin, tazobactam+piperacillin, teicoplanin, telithromycin, tigecyclin, vancomycin and combinations thereof.

Antiseptics which are suitable for use in the invention include, e.g., triclosan, phenoxy isopropanol, chlorhexidine gluconate, povidone iodine, and any combination thereof.

Antioxidative compounds may also be included in the composition, in particular the antioxidative compounds collectively termed catechins. These include for example, epicatechin, epicatechin gallate, epigallocatechin gallate, and gallocatechin, as well as stereoisomers and enantiomers of these compounds and combinations thereof. Such compounds may be provided as synthetic compounds or in the forms of mixtures as components of plant extracts, in particular green tea extracts. Botanical products and extracts include those derived from peppermint, ginger horseradish, yarrow, chamomile, rosemary, capsicum, aloe vera, tea tree oil (melaleuca oil), among many others.

A topical composition of the present invention may further include protectant active ingredients. The protectant active ingredients can be selected from the group consisting of aluminum hydroxide gel, cocoa butter, aqueous solution of glycerin, hard fat, kaolin, lanolin, mineral oil, petrolatum, topical starch, white petrolatum, cod liver, shark liver oil, and a combination thereof. The protectant active ingredient and the dosage thereof is dependent upon the particular condition to be treated, the pharmaceutical active agents present in the composition and other factors evident to those skilled in the art.

A topical composition of the present invention may include one or more of the following additional ingredients: emulsifiers (e.g. anionic, cationic or nonionic), chelating agents, colorants, emollients, fragrances, humectants, lubricants, moisturizers, preservatives, skin penetration enhancers, stabilizers, thickeners, and viscosity modifiers.

Formulations

According to an embodiment, a topical composition of the present invention comprises: (i) trimethylsiloxysilicate; (ii) at least one surfactant selected from the group consisting of sodium lauryl sulfate, alkyl- and alkoxy-dimethicone copolyol, polysorbate and a combination thereof; (iii) a non-polar volatile siloxane solvent, and (iv) a pharmaceutical agent selected from the group consisting of pramoxine, phenylephrine, hydrocortisone, salicylic acid, nitroglycerine, sildenafil, or their salts and combinations thereof. In an embodiment, the composition further comprises from about 15% (w/w) to about 40% (w/w) of water. In an embodiment, the composition further comprises a buffer to adjust the pH of the composition to a pH of about 4.2-4.4. In an embodiment, the composition further comprises a viscosity modifier.

According to an embodiment, a topical composition of the present invention comprises: (i) from about 10.0% (w/w) to about 30.0% (w/w) of trimethylsiloxysilicate; (ii) from about 1.0% (w/w) to about 5.0% (w/w) of at least one surfactant selected from the group consisting of sodium lauryl sulfate, alkyl- and alkoxy-dimethicone copolyol, polysorbate and a combination thereof; (iii) from about 30.0% (w/w) to about 75.0% (w/w) of a non-polar volatile siloxane solvent, and (iv) from about 0.005% (w/w) to about 25.0% (w/w) of a pharmaceutical agent selected from the group consisting of pramoxine, phenylephrine, hydrocortisone, salicylic acid, nitroglycerine, sildenafil, or their salts and combinations thereof. In an embodiment, the composition further comprises from about 15% (w/w) to about 40% (w/w) of water. In an embodiment, the composition further comprises a buffer to adjust the pH of the composition to a pH of about 4.2-4.4. In an embodiment, the composition further comprises a viscosity modifier.

According to an embodiment, a topical composition of the present invention comprises: (i) a silicone resin film forming agent comprising siloxysilicate, silsesquioxane, or a derivative or a combination thereof; (ii) an anionic surfactant; (iii) a volatile solvent, (iv) water; and (v) at least one pharmaceutical agent.

According to an embodiment, a topical composition of the present invention comprises: (i) a silicone resin film forming agent comprising siloxysilicate, silsesquioxane, or a derivative or a combination thereof; (ii) an anionic surfactant; (iii) a nonionic surfactant, (iv) a volatile solvent, (v) water; and (vi) at least one pharmaceutical agent.

According to an embodiment, a topical composition of the present invention comprises: (i) a silicone resin film forming agent comprising siloxysilicate, silsesquioxane, or a derivative or a combination thereof; (ii) a nonionic surfactant; (iii) a volatile solvent, (iv) water; and (v) at least one pharmaceutical agent.

According to an embodiment, a topical composition of the present invention comprises: (i) a silicone resin film forming agent comprising siloxysilicate, silsesquioxane, or a derivative or a combination thereof; (ii) an anionic surfactant; (iii) a volatile solvent, (iv) water; (v) gelling agent; and (vi) at least one pharmaceutical agent.

According to an embodiment, a topical composition of the present invention comprises: (i) a silicone resin film forming agent comprising siloxysilicate, silsesquioxane, or a derivative or a combination thereof; (ii) an anionic surfactant; (iii) a nonionic surfactant, (iv) a volatile solvent, (v) water; (vi) gelling agent; and (vii) at least one pharmaceutical agent.

According to an embodiment, a topical composition of the present invention comprises: (i) a silicone resin film forming agent comprising siloxysilicate, silsesquioxane, or a derivative or a combination thereof; (ii) a nonionic surfactant; (iii) a volatile solvent, (iv) water; (v) gelling agent; and (vi) at least one pharmaceutical agent.

According to an embodiment, a topical composition of the present invention comprises: (i) trimethylsiloxysilicate; (ii) sodium alkyl sulfate; (iii) a volatile solvent, selected from the group consisting of methylsiloxane, a polydimethylsiloxane, aliphatic hydrocarbon and a combination thereof; (iv) water; and (v) at least one pharmaceutical agent.

According to an embodiment, a topical composition of the present invention comprises: (i) trimethylsiloxysilicate; (ii) sodium lauryl sulfate; (iii) a volatile solvent, selected from the group consisting of methylsiloxane, hexamethyldisiloxane, isooctane and a combination thereof; (iv) water; and (v) at least one pharmaceutical agent.

According to an embodiment, a topical composition of the present invention comprises: (i) trimethylsiloxysilicate; (ii) sodium alkyl sulfate; (iii) alkyl- and alkoxy-dimethicone copolyol; (iv) a volatile solvent, selected from the group consisting of methylsiloxane, a polydimethylsiloxane, aliphatic hydrocarbon and a combination thereof; (v) water; and (vi) at least one pharmaceutical agent.

According to an embodiment, a topical composition of the present invention comprises: (i) trimethylsiloxysilicate; (ii) sodium lauryl sulfate; (iii) Cetyl PEG/PPG-10/1 Dimethicone; (iv) a volatile solvent, selected from the group consisting of methylsiloxane, hexamethyldisiloxane, isooctane and a combination thereof; (v) water; and (vi) at least one pharmaceutical agent.

According to an embodiment, a topical composition of the present invention comprises: (i) trimethylsiloxysilicate; (ii) polysorbate; (iii) alkyl- and alkoxy-dimethicone copolyol; (iv) a volatile solvent, selected from the group consisting of methylsiloxane, polydimethylsiloxane, aliphatic hydrocarbon and a combination thereof; (v) water; and (vi) at least one pharmaceutical agent.

According to an embodiment, a topical composition of the present invention comprises: (i) trimethylsiloxysilicate; (ii) Tween 80; (iii) Cetyl PEG/PPG-10/1 Dimethicone; (iv) a volatile solvent, selected from the group consisting of methylsiloxane, hexamethyldisiloxane, isooctane and a combination thereof; (v) water; and (vi) at least one pharmaceutical agent.

According to an embodiment, a topical composition of the present invention comprises: (i) trimethylsiloxysilicate; (ii) sodium alkyl sulfate; (iii) a volatile solvent, selected from the group consisting of methylsiloxane, a polydimethylsiloxane, aliphatic hydrocarbon and a combination thereof; (iv) water; (v) cellulose derivatives at least one pharmaceutical agent.

According to an embodiment, a topical composition of the present invention comprises: (i) trimethylsiloxysilicate; (ii) sodium lauryl sulfate; (iii) a volatile solvent, selected from the group consisting of methylsiloxane, hexamethyldisiloxane, isooctane and a combination thereof; (iv) water; (v) hydroxypropyl methyl cellulose; and (vi) at least one pharmaceutical agent.

According to an embodiment, a topical composition of the present invention comprises: (i) a silicone resin film forming agent comprising siloxysilicate, silsesquioxane, or a derivative or a combination thereof; (ii) a surfactant; (iii) a volatile solvent, (iv) water; (v) at least one pharmaceutical agent; (vi) a dimethicone/vinyldimethicone crosspolymer; and (vii) a silicone gum blend.

According to an embodiment, a topical composition of the present invention comprises: (i) a silicone resin film forming agent comprising siloxysilicate, silsesquioxane, or a derivative or a combination thereof; (ii) a surfactant; (iii) a volatile solvent, (iv) water; (v) at least one pharmaceutical agent; (vi) a dimethicone/vinyldimethicone crosspolymer; (vii) a silicone gum blend; and (ix) a gelling agent.

According to an embodiment, a topical composition of the present invention comprises: (i) a silicone resin film forming agent comprising siloxysilicate, silsesquioxane, or a derivative or a combination thereof; (ii) anionic surfactant; (iii) a volatile solvent, (iv) water; (v) at least one pharmaceutical agent; (vi) a dimethicone/vinyldimethicone crosspolymer; and (vii) a silicone gum blend.

According to an embodiment, a topical composition of the present invention comprises: (i) a silicone resin film forming agent comprising siloxysilicate, silsesquioxane, or a derivative or a combination thereof; (ii) anionic surfactant; (iii) a volatile solvent, (iv) water; (v) at least one pharmaceutical agent; (vi) a dimethicone/vinyldimethicone crosspolymer; (vii) a silicone gum blend; and (ix) a gelling agent.

According to an embodiment, a topical composition of the present invention comprises: (i) a silicone resin film forming agent; (ii) anionic surfactant; (iii) nonionic surfactant; (iv) a volatile solvent, (v) water; (vi) at least one pharmaceutical agent; (vii) a dimethicone/vinyldimethicone crosspolymer; and (viii) a silicone gum blend.

According to an embodiment, a topical composition of the present invention comprises: (i) a silicone resin film forming agent comprising siloxysilicate, silsesquioxane, or a derivative or a combination thereof; (ii) anionic surfactant; (Iii) nonionic surfactant; (iv) a volatile solvent, (v) water; (vi) at least one pharmaceutical agent; (vii) a dimethicone/vinyldimethicone crosspolymer; (viii) a silicone gum blend; and (ix) a gelling agent.

According to an embodiment, a topical composition of the present invention comprises: (i) a silicone resin film forming agent comprising siloxysilicate, silsesquioxane, or a derivative or a combination thereof; (ii) nonionic surfactant; (iii) a volatile solvent, (iv) water; (v) at least one pharmaceutical agent; (vi) a dimethicone/vinyldimethicone crosspolymer; and (vii) a silicone gum blend.

According to an embodiment, a topical composition of the present invention comprises: (i) a silicone resin film forming agent comprising siloxysilicate, silsesquioxane, or a derivative or a combination thereof; (ii) nonionic surfactant; (iii) a volatile solvent, (iv) water; (v) at least one pharmaceutical agent; (vi) a dimethicone/vinyldimethicone crosspolymer; (vii) a silicone gum blend; and (ix) a gelling agent.

According to an embodiment, a topical composition of the present invention comprises: (i) trimethylsiloxysilicate; (ii) sodium alkyl sulfate; (iii) a volatile solvent, selected from the group consisting of methylsiloxane, a polydimethylsiloxane, aliphatic hydrocarbon and a combination thereof; (iv) water; (v) at least one pharmaceutical agent; (vi) bis-vinyldimethicone, vinyldimethicone and hydrogen dimethicone; and (vii) dimethiconol and silicone oil blend.

According to an embodiment, a topical composition of the present invention comprises: (i) trimethylsiloxysilicate; (ii) sodium alkyl sulfate; (iii) a volatile solvent, selected from the group consisting of methylsiloxane, a polydimethylsiloxane, aliphatic hydrocarbon and a combination thereof; (iv) water; (v) at least one pharmaceutical agent; (vi) bis-vinyldimethicone, vinyldimethicone and hydrogen dimethicone; (vii) dimethiconol and silicone oil blend; and (iv) cellulose derivative.

According to an embodiment, a topical composition of the present invention comprises: (i) trimethylsiloxysilicate; (ii) sodium alkyl sulfate; (iii) alkyl- and alkoxy-dimethicone copolyol; (iv) a volatile solvent, selected from the group consisting of methylsiloxane, a polydimethylsiloxane, aliphatic hydrocarbon and a combination thereof; (v) water; (vi) at least one pharmaceutical agent; (vii) bis-vinyldimethicone, vinyldimethicone and hydrogen dimethicone; and (viii) dimethiconol and silicone oil blend.

According to an embodiment, a topical composition of the present invention comprises: (i) trimethylsiloxysilicate; (ii) sodium alkyl sulfate; (iii) alkyl- and alkoxy-dimethicone copolyol; (iv) a volatile solvent, selected from the group consisting of methylsiloxane, a polydimethylsiloxane, aliphatic hydrocarbon and a combination thereof; (v) water; (vi) at least one pharmaceutical agent; (vii) bis-vinyldimethicone, vinyldimethicone and hydrogen dimethicone; (viii) dimethiconol and silicone oil blend; and (ix) cellulose derivative.

According to an embodiment, a topical composition of the present invention comprises: (i) trimethylsiloxysilicate; (ii) polysorbate; (iii) alkyl- and alkoxy-dimethicone copolyol; (iv) a volatile solvent, selected from the group consisting of methylsiloxane, a polydimethylsiloxane, aliphatic hydrocarbon and a combination thereof; (v) water; (vi) at least one pharmaceutical agent; (vii) bis-vinyldimethicone, vinyldimethicone and hydrogen dimethicone; and (viii) dimethiconol and silicone oil blend.

According to an embodiment, a topical composition of the present invention comprises: (i) trimethylsiloxysilicate; (ii) polysorbate; (iii) alkyl- and alkoxy-dimethicone copolyol; (iv) a volatile solvent, selected from the group consisting of methylsiloxane, a polydimethylsiloxane, aliphatic hydrocarbon and a combination thereof; (v) water; (vi) at least one pharmaceutical agent; (vii) bis-vinyldimethicone, vinyldimethicone and hydrogen dimethicone; (viii) dimethiconol and silicone oil blend; and (ix) cellulose derivative.

According to an embodiment, a topical composition of the present invention comprises: (i) trimethylsiloxysilicate; (ii) sodium lauryl sulfate; (iii) a volatile solvent, selected from the group consisting of methylsiloxane, hexamethyldisiloxane, isooctane and a combination thereof; (iv) water; (v) at least one pharmaceutical agent, selected from the group consisting of an anesthetic agent, a vasoconstrictor, an antipruritic agent, an immunomodulator, a cytotoxin, an anti-inflammatory agent, a muscle relaxant, and a combination thereof; (vi) bis-vinyldimethicone, vinyldimethicone and hydrogen dimethicone; and (vii) cyclopentasiloxane and dimethiconol.

According to an embodiment, a topical composition of the present invention comprises: (i) trimethylsiloxysilicate; (ii) sodium lauryl sulfate; (iii) a volatile solvent, selected from the group consisting of methylsiloxane, hexamethyldisiloxane, isooctane and a combination thereof; (iv) water; (v) at least one pharmaceutical agent, selected from the group consisting of an anesthetic agent, a vasoconstrictor, an antipruritic agent, an immunomodulator, a cytotoxin, an anti-inflammatory agent, a muscle relaxant, and a combination thereof; (vi) bis-vinyldimethicone, vinyldimethicone and hydrogen dimethicone; (vii) cyclopentasiloxane and dimethiconol; and (iv) hydroxypropyl methyl cellulose.

According to an embodiment, a topical composition of the present invention comprises: (i) trimethylsiloxysilicate; (ii) sodium lauryl sulfate; (iii) Cetyl PEG/PPG-10/1 Dimethicone; (iv) a volatile solvent, selected from the group consisting of methylsiloxane, hexamethyldisiloxane, isooctane and a combination thereof; (v) water; (vi) at least one pharmaceutical agent selected from the group consisting of an anesthetic agent, a vasoconstrictor, an antipruritic agent, an anti-inflammatory agent, a muscle relaxant, or a combination thereof; (vii) bis-vinyldimethicone, vinyldimethicone and hydrogen dimethicone; and (viii) cyclopentasiloxane and dimethiconol.

According to an embodiment, a topical composition of the present invention comprises: (i) trimethylsiloxysilicate; (ii) sodium lauryl sulfate; (iii) Cetyl PEG/PPG-10/1 Dimethicone; (iv) a volatile solvent, selected from the group consisting of hexamethyldisiloxane, isooctane and a combination thereof; (v) water; (vi) at least one pharmaceutical agent selected from the group consisting of an anesthetic agent, a vasoconstrictor, an immunomodulator, a cytotoxin, an antipruritic agent, an anti-inflammatory agent, a muscle relaxant, or a combination thereof; (vii) bis-vinyldimethicone, vinyldimethicone and hydrogen dimethicone; (viii) cyclopentasiloxane and dimethiconol; and (ix) hydroxypropyl methyl cellulose.

According to an embodiment, a topical composition of the present invention comprises: (i) trimethylsiloxysilicate; (ii) Tween 80; (iii) Cetyl PEG/PPG-10/1 Dimethicone; (iv) a volatile solvent, selected from the group consisting of methylsiloxane, hexamethyldisiloxane, isooctane and a combination thereof; (v) water; (vi) at least one pharmaceutical agent selected from the group consisting of an anesthetic agent, a vasoconstrictor, an antipruritic agent, an anti-inflammatory agent, a muscle relaxant, an immunomodulator, a cytotoxin, or a combination thereof; (vii) bis-vinyldimethicone, vinyldimethicone and hydrogen dimethicone; and (viii) cyclopentasiloxane and dimethiconol.

According to an embodiment, a topical composition of the present invention comprises: (i) trimethylsiloxysilicate; (ii) Tween 80; (iii) Cetyl PEG/PPG-10/1 Dimethicone; (iv) a volatile solvent, selected from the group consisting of methylsiloxane, hexamethyldisiloxane, isooctane and a combination thereof; (v) water; (vi) at least one pharmaceutical agent selected from the group consisting of an anesthetic agent, a vasoconstrictor, an antipruritic agent, an anti-inflammatory agent, a muscle relaxant, an immunomodulator, a cytotoxin, or a combination thereof; (vii) bis-vinyldimethicone, vinyldimethicone and hydrogen dimethicone; (viii) cyclopentasiloxane and dimethiconol; and (ix) hydroxypropyl methyl cellulose.

According to an embodiment, a topical composition of the present invention comprises: (i) about 10-40% (w/w) of a silicone resin film forming agent comprising siloxysilicate, silsesquioxane, or a derivative or a combination thereof; (ii) about 0.5% (w/w) to about 7% (w/w) of a surfactant; (iii) about 30% (w/w) to about 80% (w/w) of a volatile solvent; (iv) about 20% (w/w) to about 40% (w/w) of water; and (v) about 0.005% (w/w) to about 25% (w/w) of at least one pharmaceutical agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 2.5% (w/w) of an anionic surfactant; (iii) about 30% (w/w) to about 80% (w/w) of a volatile solvent; (iv) about 15% (w/w) to about 40% (w/w) of water; and (v) about 0.005% (w/w) to about 25% (w/w) of at least one pharmaceutical agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 2.5% (w/w) of an anionic surfactant; (iii) about 30% (w/w) to about 80% (w/w) of a volatile solvent; (iv) about 20% (w/w) to about 40% (w/w) of water; (v) about 0.005% (w/w) to about 25% (w/w) of at least one pharmaceutical agent; and (vi) about 0.05% (w/w) to about 5.0% (w/w) gelling agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 2.5% (w/w) of an anionic surfactant; (iii) about 2% (w/w) to about 7% (w/w) of a nonionic surfactant; (iv) about 30% (w/w) to about 50% (w/w) of a volatile solvent; (v) about 25% (w/w) to about 40% (w/w) of water; and (vi) about 0.005% (w/w) to about 25% (w/w) of at least one pharmaceutical agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 2.5% (w/w) of an anionic surfactant; (iii) about 2% (w/w) to about 7% (w/w) of a nonionic surfactant; (iv) about 30% (w/w) to about 80% (w/w) of a volatile solvent; (v) about 20% (w/w) to about 40% (w/w) of water; (vi) about 0.005% (w/w) to about 25% (w/w) of at least one pharmaceutical agent and (vii) about 0.05% (w/w) to about 5.0% (w/w) gelling agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 7.0% (w/w) of a nonionic surfactant; (iii) about 30% (w/w) to about 80% (w/w) of a volatile solvent; (iv) about 20% (w/w) to about 40% (w/w) of water; and (v) about 0.005% (w/w) to about 25% (w/w) of at least one pharmaceutical agent.

According to an embodiment, a topical composition of the present invention comprises: (i) about 10% (w/w) to about 40% (w/w) of a silicone resin film forming agent comprising siloxysilicate, silsesquioxane, or a derivative or a combination thereof; (ii) about 0.5% (w/w) to about 7.0% (w/w) of a nonionic surfactant; (iii) about 30% (w/w) to about 80%

(w/w) of a volatile solvent; (iv) about 20% (w/w) to about 40% (w/w) of water; (v) about 0.005% (w/w) to about 25% (w/w) of at least one pharmaceutical agent; and (vi) about 0.05% (w/w) to about 5% (w/w) gelling agent.

According to an embodiment, a topical composition of the present invention comprises: (i) about 10% (w/w) to about 40% (w/w) of trimethylsiloxysilicate; (ii) about 0.5% (w/w) to about 2.5% (w/w) of sodium alkyl sulfate; (iii) about 30% (w/w) to about 80% (w/w) of a volatile solvent, selected from the group consisting of methylsiloxane, a polydimethylsiloxane, aliphatic hydrocarbon and a combination thereof; (iv) about 15% (w/w) to about 40% (w/w) of water; (v) about 0.005% (w/w) to about 25% (w/w) of at least one pharmaceutical agent, selected from the group consisting of an anesthetic agent, a vasoconstrictor, an antipruritic agent, an anti-inflammatory agent, a muscle relaxant, or a combination thereof; (vi) about 5.0% (w/w) to about 15% (w/w) bis-vinyldimethicone, vinyldimethicone and hydrogen dimethicone; and (vii) about 0.5% (w/w) to about 2.5% (w/w) dimethiconol and silicone oil blend.

According to an embodiment, a topical composition of the present invention comprises: (i) about 10% (w/w) to about 40% (w/w) of trimethylsiloxysilicate; (ii) about 0.5% (w/w) to about 2.5% (w/w) of sodium alkyl sulfate; (iii) about 30% (w/w) to about 80% (w/w) of a volatile solvent, selected from the group consisting of methylsiloxane, a polydimethylsiloxane, aliphatic hydrocarbon and a combination thereof; (iv) about 15% (w/w) to about 40% (w/w) of water; (v) about 0.005% (w/w) to about 25% (w/w) of at least one pharmaceutical agent, selected from the group consisting of an anesthetic agent, a vasoconstrictor, an antipruritic agent, an anti-inflammatory agent, a muscle relaxant, or a combination thereof; (vi) about 5.0% (w/w) to about 15% (w/w) bis-vinyldimethicone, vinyldimethicone and hydrogen dimethicone; (vii) about 0.5% (w/w) to about 2.5% (w/w) dimethiconol and silicone oil blend; and (viii) about 0.05% (w/w) to about 5.0% (w/w) cellulose derivative.

According to an embodiment, a topical composition of the present invention comprises: (i) about 10% (w/w) to about 40% (w/w) of trimethylsiloxysilicate; (ii) about 0.5% (w/w) to about 2.5% (w/w) of sodium alkyl sulfate; (iii) about 2.0% (w/w) to about 7% (w/w) of alkyl- and alkoxy-dimethicone copolyol; (iv) about 30% (w/w) to about 80% (w/w) of a volatile solvent, selected from the group consisting of methylsiloxane, a polydimethylsiloxane, aliphatic hydrocarbon and a combination thereof; (v) about 15% (w/w) to about 40% (w/w) of water; (vi) about 0.005% (w/w) to about 25% (w/w) of at least one pharmaceutical agent, selected from the group consisting of an anesthetic agent, a vasoconstrictor, an antipruritic agent, an anti-inflammatory agent, a muscle relaxant, or a combination thereof; (vii) about 5.0% (w/w) to about 15% (w/w) bis-vinyldimethicone, vinyldimethicone and hydrogen dimethicone; and (viii) about 0.5% (w/w) to about 2.5% (w/w) dimethiconol and silicone oil blend.

According to an embodiment, a topical composition of the present invention comprises: (i) about 10% (w/w) to about 40% (w/w) of trimethylsiloxysilicate; (ii) about 0.5% (w/w) to about 2.5% (w/w) of sodium alkyl sulfate; (iii) about 2.0% (w/w) to about 7% (w/w) of alkyl- and alkoxy-dimethicone copolyol; (iv) about 30% (w/w) to about 80% (w/w) of a volatile solvent, selected from the group consisting of methylsiloxane, a polydimethylsiloxane, aliphatic hydrocarbon and a combination thereof; (v) about 15% (w/w) to about 40% (w/w) of water; (vi) about 0.005% (w/w) to about 25% (w/w) of at least one pharmaceutical agent, selected from the group consisting of an anesthetic agent, a vasoconstrictor, an antipruritic agent, an anti-inflammatory agent, a muscle relaxant, or a combination thereof; (vii) about 5.0% (w/w) to about 15% (w/w) bis-vinyldimethicone, vinyldimethicone and hydrogen dimethicone; (viii) about 0.5% (w/w) to about 2.5% (w/w) dimethiconol and silicone oil blend and (viii) about 0.05% (w/w) to about 5% (w/w) cellulose derivative.

According to an embodiment, a topical composition of the present invention comprises: (i) about 10% (w/w) to about 40% (w/w) of trimethylsiloxysilicate; (ii) about 0.5% (w/w) to about 2.5% (w/w) of polysorbate; (iii) about 2.0% (w/w) to about 7% (w/w) of alkyl- and alkoxy-dimethicone copolyol; (iv) about 30% (w/w) to about 80% (w/w) of a volatile solvent, selected from the group consisting of methylsiloxane, a polydimethylsiloxane, aliphatic hydrocarbon and a combination thereof; (v) about 15% (w/w) to about 40% (w/w) of water; (vi) about 0.005% (w/w) to about 25% (w/w) of at least one pharmaceutical agent, selected from the group consisting of an anesthetic agent, a vasoconstrictor, an antipruritic agent, an immunomodulator, a muscle relaxant, or a combination thereof; (vii) about 5.0% (w/w) to about 15% (w/w) bis-vinyldimethicone, vinyldimethicone and hydrogen dimethicone; and (viii) about 0.5% (w/w) to about 2.5% (w/w) dimethiconol and silicone oil blend.

According to an embodiment, a topical composition of the present invention comprises: (i) about 10% (w/w) to about 40% (w/w) of trimethylsiloxysilicate; (ii) about 0.5% (w/w) to about 2.5% (w/w) of polysorbate; (iii) about 2.0% (w/w) to about 7.0% (w/w) of alkyl- and alkoxy-dimethicone copolyol; (iv) about 30% (w/w) to about 80% (w/w) of a volatile solvent, selected from the group consisting of methylsiloxane, a polydimethylsiloxane, aliphatic hydrocarbon and a combination thereof; (v) about 15.0% (w/w) to about 40% (w/w) of water; (vi) about 0.005% (w/w) to about 25% (w/w) of at least one pharmaceutical agent, selected from the group consisting of an anesthetic agent, a vasoconstrictor, an antipruritic agent, a keratolytic, a protectant, an anti-inflammatory agent, an astringent, a muscle relaxant, or a combination thereof; (vii) about 5.0% (w/w) to about 15% (w/w) bis-vinyldimethicone, vinyldimethicone and hydrogen dimethicone; (viii) about 0.5% (w/w) to about 2.5% (w/w) dimethiconol and silicone oil blend and (viii) about 0.05% (w/w) to about 5% (w/w) cellulose derivative.

According to an embodiment, a topical composition of the present invention comprises: (i) about 15% (w/w) trimethylsiloxysilicate; (ii) about 3% (w/w) sodium lauryl sulfate; (iii) about 22% (w/w) hexamethyldisiloxane and 21% (w/w) isooctane; (iv) about 27% (w/w) water or citrate buffer or a combination thereof; (v) about 1% (w/w) pramoxine; (vi) about 0.25% (w/w) phenylephrine; (vii) about 5% (w/w) bis-vinyldimethicone and 5% (w/w) vinyldimethicone and hydrogen dimethicone; and (viii) about 1% (w/w) cyclopentasiloxane and dimethiconol.

According to an embodiment, a topical composition of the present invention comprises: (i) about 15% (w/w) trimethylsiloxysilicate; (ii) about 3% (w/w) sodium lauryl sulfate; (iii) about 22% (w/w) hexamethyldisiloxane and 21% (w/w) isooctane; (iv) about 27% (w/w) water or citrate buffer or a combination thereof; (v) about 1% (w/w) pramoxine; (vi) about 0.25% (w/w) phenylephrine; (vii) about 5% (w/w) bis-vinyldimethicone and 5% (w/w) vinyldimethicone and hydrogen dimethicone; (viii) about 1% (w/w) cyclopentasiloxane and dimethiconol; and (ix) about 0.5% (w/w) hydroxypropyl methyl cellulose According to an embodiment, a topical composition of the present invention comprises: (i) about 15% (w/w) trimethylsiloxysilicate; (ii) about 1.5% (w/w) sodium lauryl sulfate; (iii) about 4% (w/w) Ceti PEG/PPG-10/i Dimethicone; (iv) about 22% (w/w) hexamethyldisiloxane and 21% (w/w)

isooctane; (v) about 25% (w/w) water; (vi) about 1% (w/w) pramoxine; (vii) about 0.25% (w/w) phenylephrine; (viii) about 5% (w/w) bis-vinyldimethicone and 5% (w/w) vinyldimethicone and hydrogen dimethicone; and (ix) about 1% (w/w) cyclopentasiloxane and dimethiconol.

According to an embodiment, a topical composition of the present invention comprises: (i) about 15% (w/w) trimethylsiloxysilicate; (ii) about 1.5% (w/w) sodium lauryl sulfate; (iii) about 4% (w/w) Cetyl PEG/PPG-10/1 Dimethicone; (iv) about 18% (w/w) hexamethyldisiloxane and 19% (w/w) isooctane; (v) about 30% (w/w) water; (vi) about 1% (w/w) pramoxine; (vii) about 0.25% (w/w) phenylephrine; (viii) about 5% (w/w) bis-vinyldimethicone and 5% (w/w) vinyldimethicone and hydrogen dimethicone; (ix) about 1% (w/w) cyclopentasiloxane and dimethiconol; and (x) about 0.5% (w/w) hydroxypropyl methyl cellulose.

According to an embodiment, a topical composition of the present invention comprises: (i) about 15% (w/w) trimethylsiloxysilicate; (ii) about 1.5% (w/w) Tween 80; (iii) about 4% (w/w) Cetyl PEG/PPG-10/1 Dimethicone; (iv) about 22% (w/w) hexamethyldisiloxane and 21% (w/w) isooctane; (v) about 25% (w/w) water; (vi) about 1% (w/w) pramoxine; (vii) about 0.25% (w/w) phenylephrine; (viii) about 5% (w/w) bis-vinyldimethicone and 5% (w/w) vinyldimethicone and hydrogen dimethicone; and (ix) about 1% (w/w) cyclopentasiloxane and dimethiconol.

According to an embodiment, a topical composition of the present invention comprises: (i) about 15% (w/w) trimethylsiloxysilicate; (ii) about 1.5% (w/w) Tween 80; (iii) about 4% (w/w) Cetyl PEG/PPG-10/1 Dimethicone; (iv) about 18% (w/w) hexamethyldisiloxane and 19% (w/w) isooctane; (v) about 30% (w/w) water; (vi) about 1% (w/w) pramoxine; (vii) about 0.25% (w/w) phenylephrine; (viii) about 5% (w/w) bis-vinyldimethicone and 5% (w/w) vinyldimethicone and hydrogen dimethicone; (ix) about 1% (w/w) cyclopentasiloxane and dimethiconol; and (x) about 0.5% (w/w) hydroxypropyl methyl cellulose.

According to an embodiment, a topical composition of the present invention in the form of a gel (see composition L in Table 2), comprises: (i) about 25% (w/w) trimethylsiloxysilicate (ii) about 43% (w/w) methylsiloxane (iii) about 4% (w/w) Cetyl PEG/PPG-10/1 Dimethicone (iv) about 1.5% (w/w) Tween 80 (v) about 25% (w/w) water, (vi) about 1% (w/w) pramoxine hydrochloride (vii) about 0.25% (w/w) phenylephrine hydrochloride and (viii) about 0.6% (w/w) Hydroxyethylcellulose (Natrosol HHX).

According to an embodiment, a topical composition of the present invention (see composition H1 in Table 1, Example 1 in the form of an oil-in-water emulsion liquid) comprises: (i) about 25% (w/w) trimethylsiloxysilicate (ii) about 38% (w/w) methylsiloxane (0.54 cP) (iii) about 4% (w/w) Cetyl PEG/PPG-10/1 Dimethicone (iv) about 3% (w/w) Tween 80 (v) about 30% (w/w) acetate buffer pH 4.4 (vi) about 1% (w/w) pramoxine HCl and (vii) about 0.25% (w/w) phenylephrine HCl.

According to an embodiment, a topical composition of the present invention see composition H2 in Table 1, Example 1 in the form of an oil-in-water emulsion liquid) comprises: (i) about 15% (w/w) trimethylsiloxysilicate (ii) about 47% (w/w) methylsiloxane (0.54 cP) (iii) about 4% (w/w) Cetyl PEG/PPG-10/1 Dimethicone (iv) about 3% (w/w) Tween 80 (v) about 20% (w/w) acetate buffer pH 4.4 (vi) about 1% (w/w) pramoxine HCl and (vii) about 0.25% (w/w) phenylephrine HCl and (viii) about 0.01% (w/w) to about 0.1% (w/w) Pemulen TR-1.

Containers and Applicators

The compositions for use in the present invention are generally stored in a container-applicator device for use in a single dose application (e.g., a wipe or a swab in a disposable container) or for use in repeated applications to the anus and rectum. Single dose applicators include those having breakable or removable seals that prevent moisture, including atmospheric moisture, from contacting the formulation.

In an embodiment of the invention, a topical water-based composition is in the form of a pre-packaged towelette/wipe. The wipe substrate is typically uniformly impregnated with the topical water-based composition. According to an embodiment, the topical water-based composition is in a liquid form, when applied to the wipe. According to an embodiment, the topical water-based composition is in a gel form, when applied to a wipe. The wipe provides the user with a single dose of sterile medication. The topical composition is transferred to the body surface upon contacting the wipe with the target surface.

The design of wipes is well known to those of skill in the art. Each wipe is generally packaged as a single-use sealed unit. The wipe is formed of woven or non-woven fabric, cloth or tissue substrate and the impregnated wipe may be sealed into an enveloping sachet or pocket. In an embodiment, the sachet or pocket is formed by sandwiching a folded and impregnated wipe between two sheets of an aluminum foil/polyethylene film laminate. The sheets of laminate may comprise folded over portions of a single sheet of such material.

A container-applicator may further comprise two parts: (1) a storage area or reservoir which holds the composition and protects it from air, water and contaminants; and (2) the applicator which generally comprises a specially shaped tip designed to aid in application of the composition to the anal and/or rectal mucosa. In particular embodiments, the applicator is an element integral to the container, for example, an elongated insertion tube extending from a reservoir. Alternately, the storage area and the applicator may be separate components, such as a tube reservoir and a separately supplied dropper. In yet other embodiments, the container and the applicator may be supplied as separate elements which are connected during use, for example via compatible male and female connectors respectively provided on the container and the applicator or vice versa.

For repeated and intermittent usage, minimal exposure to atmospheric moisture is required. This can be achieved by devices having very narrow applicator outlets and low initial dead space. One applicator for such repeated intermittent use dispenses the composition in a controlled drop wise manner, as described for example in U.S. Pat. No. 4,958,748.

Still another container-applicator device comprises a brush or solid paddle applicator wherein the topical composition is "painted" onto the surface requiring treatment.

The container-applicator device for repeated and intermittent usage may comprise a container suitable for non-sterile storage of the composition, and an applicator suitable for metered dispensing of the composition after opening of the applicator. In particular embodiments, the applicator is characterized as having a resealable opening of no more than about 0.05 square inch (0.323 square centimeters) so as to permit the metered dispersement of the composition from the applicator and which is capable of multiple administrations of the composition, and is further characterized as having resealing means such as a cap which either tightly mates with the applicator or which screws onto the applicator. The opening may be at the terminus of an elongated and tapered tube-like member suitable for insertion into the anal canal and accessing internal hemorrhoids. In an embodiment, the opening of the applicator is about 0.001 to about 0.01 square inch (about 0.00645 to about 0.0645 square centimeters).

In an embodiment, the walls of the container-applicator device are made of a pliable material, so that upon application of pressure onto the walls, the walls depress sufficiently to force the composition in the container into the applicator and through the opening. In another embodiment, the composition is released from the applicator by gravity feed methods well known in the art. Such methods do not require application of pressure to the walls of the container.

In an embodiment, the applicator is manufactured with its opening covered by a metal foil or other similar construction which closes this opening until the device is ready for use. The opening is then reinstated by use of a pin or similar device which punctures the covering.

Such devices for intermittent use enable multiple uses of the topical composition at different points in time by the same individual.

In container-applicator devices suitable for repeated intermittent uses, the topical composition is stored at ambient conditions and is selected to be bacteriostatic (see, for example, U.S. Pat. No. 3,527,224). When the selected composition is bacteriostatic, prolonged storage at ambient conditions can be achieved without regard to the sterility of the formulation because there is no adverse buildup of bacteria during storage.

The reservoir of the container-applicator device may be both air-tight and water-tight, and keeps the media within free from contaminants. The reservoir may contain a desiccant material to keep the media free of water. Reservoirs may be of any shape, although shapes which provide for a smooth internal flow of media, such as cylindrical or conical shapes. The size of the reservoir may vary within a wide range, but is typically slightly larger than the volume of composition which will be placed inside the reservoir to minimize the amount of gas within the reservoir. The reservoir may be made from any of a variety of medical grade materials, such as plastics, excluding glass. Pharmaceutical agents of the topical composition suffer from caking when stored in glass reservoir. The reservoir may be rigid, collapsible, or compressible. Use of a compressible or collapsible reservoir allows the user to have greater control over the rate at which the composition is expressed, as exertion of pressure on a compressible or collapsible reservoir would place a force on the on the composition causing it to flow at a faster rate than it would in the absence of such pressure. The compressible or collapsible reservoir design is especially suitable for the topical composition in the form of gel, for which the force of gravity may not be strong enough to cause a flow through an applicator sufficient to treat hemorrhoids or fissures. Collapsible reservoirs which retain their collapsed shape have the additional advantage of reducing the amount of air which enters the reservoir following use. This advantage of collapsible containers is of greater importance in multiple-use (reusable) devices, wherein media is typically kept relatively free of potential contaminants between uses.

Applicator tips can be of any of a number of shapes, sizes, and configurations. They may be fairly rigid and may be made out of any material which is compatible with the media formulation, for example plastic, excluding glass. The choice of a proper applicator tip for a given application will depend on factors such as the viscosity of the composition, the desired application rate of the composition, the nature of the anal disorder, and its severity.

The container-applicators of the present invention may be either single-use or multiple-use devices. A container or reservoir containing enough topical composition for multiple applications may be configured to accommodate replaceable tips. In such an embodiment, at the place whereon the replaceable tips connect with the reservoir, the reservoir may have a means such as a valve, septum or sealing gasket which allows the reservoir to be sealed in the absence of an applicator tip. Placing an applicator tip on the reservoir would cause the valve to open, allowing composition to flow out from the reservoir. In this manner, one reservoir containing enough composition for several applications could be used over a period of hours, days or weeks. This embodiment would also allow the user to use one reservoir with applicator tips of varying shapes and sizes chosen to best accommodate the anal disorder during the healing process.

Uses

Disorders of the anorectal region are commonly encountered among the general population, but are often inadequately unaddressed, since many patients delay or fail to seek medical attention due to embarrassment. Furthermore, many medications for such conditions fail to provide adequate relief and healing. In addition, many medications which are intended for treatment of conditions such as hemorrhoids and anal warts may be difficult to self-administer, and are unsatisfactory due to their uncomfortable sensation after application.

The present invention provides compositions which are useful for effectively treating a variety of anorectal disorders including hemorrhoids, anal fissures, anal cracks, anal fistulas, anal abscesses, and anal pruritus, wherein the compositions provide enhanced therapeutic efficacy and are associated with improved patient compliance, as compared to prior art compositions. The provided compositions may be useful for simultaneously treating a number of anorectal disorders.

Hemorrhoids (also known as piles) form part of the normal human anatomy of the anal canal, but may become pathological when swollen or inflamed. In their physiological state they act as cushions composed of arterio-venous channels and connective tissue that aid the passage of stool. The symptoms of pathological hemorrhoids include rectal bleeding, tenderness and pain in the anal area.

Pathological hemorrhoids are typically classified as external or internal, which are differentiated via their position with respect to the dentate line. External hemorrhoids occur outside the anal verge (the distal end of the anal canal) as varicosities of the veins draining the territory of the inferior rectal arteries, which are branches of the internal pudendal artery. External hemorrhoids are frequently painful, and are often accompanied by swelling, skin irritation and itching. External hemorrhoids are prone to thrombosis, which may occur if the vein ruptures and/or a blood clot develops.

Internal hemorrhoids occur within the rectum as varicosities of veins draining the territory of branches of the superior rectal arteries. As this area lacks pain receptors, internal hemorrhoids are often painless and affected individuals may be unaware of their occurrence. Internal hemorrhoids may however, bleed when irritated. Untreated internal hemorrhoids can lead to the more sever conditions of prolapsed or strangulated hemorrhoids. Prolapsed hemorrhoids are severely distended such that they are extruded outside the anus. If the anal sphincter muscle goes into spasm and traps a prolapsed hemorrhoid outside the anal opening, the supply of blood is cut off, and the hemorrhoid becomes a strangulated hemorrhoid.

Internal hemorrhoids can be further graded by the degree of prolapse, in which Grade I is characterized by the absence of prolapse; Grade II is characterized by prolapse upon defecation but which reduce spontaneously; Grade III is characterized by prolapse upon defecation, which may be manually reduced; and Grade IV is characterized by prolapse which cannot be manually reduced.

An anal fissure is a crack or tear in the skin of the anal canal. Acute cases may be associated with severe periodic pain after defecation, while chronic cases are associated with less intense pain. Anal fissures usually extend from the anal opening and are usually located posteriorly in the midline. Fissure depth may be superficial or extend down to the underlying sphincter muscle. Most anal fissures are due to stretching of the anal mucosa beyond their capability. A common cause of non-healing chronic fissures is spasm of the internal anal sphincter muscle, resulting in impaired blood supply to the anal mucosa. The result is a non-healing ulcer, which may become infected by fecal bacteria.

Non-surgical conventional treatments for acute and chronic anal fissures are generally those used for hemorrhoids. Topically applied medications used for relaxation of the sphincter muscle include nitroglycerine, nifedipine, diltiazem, verapamil, sildenafil citrate, and/or lidocaine. Surgical treatment procedures such as anal stretch (Lord's operation) or lateral sphincterotomy are aimed to decrease sphincter spasm. Another approach involves injection of botulinum toxin into the anal sphincter.

Anorectal or perianal abscess (also known as anal/rectal abscess, perianal/perirectal abscess) is an abscess occurring adjacent to the anus, due to infection at one of the anal crypts of Morgagni. Most cases are sporadic, although individuals with diabetes mellitus or Crohn's disease, or those undergoing chronic steroid treatment have increased risk and incidence. The condition is generally treated by surgery to drain the infection, followed by oral administration of antibiotics and possibly topical treatments. Anal abscess often leads to an anal fistula, which is the development of an infected channel within a gland between the anal canal and external skin near the anus or rectum. This condition also requires surgical treatment generally followed by administration of antibiotics.

Anal pruritus (also known as pruritus ani or anusitis) is an irritation of the skin at the anus, associated with intensive urge to scratch the affected area. The condition may be idiopathic, or associated with various factors or co-existing conditions, including occult or overt fecal soiling, ingestion of certain foods, bacterial or fungal infection, hemorrhoids or additional co-existing anorectal disorders, and dermatological conditions, in particular allergic contact dermatitis or psoriasis. Treatment measures include enhanced hygiene, antibiotics or antifungal medications when infections are present, various creams and ointments, generally containing local anesthetics, vasoconstrictors, protectants or combinations thereof, and topical steroids. The composition is applied to areas of the anal canal or rectum affected by hemorrhoids, fissures, fistulae, cracks, warts or pruritus, under conditions suitable for film formation of the composition so as to form a protective coating and typically under non-sterile conditions. In general, sufficient amounts of topical composition are employed to cover the entire affected mucosal surface area. In an embodiment, the coating is extended by at least about 1 centimeter and by at least about 5 centimeters beyond the affected surface area.

The term "therapeutically effective amount" as used herein means an amount of the pharmaceutical agent which is sufficient to provide a beneficial effect to the subject to which the pharmaceutical agent is administered. More specifically, a therapeutically effective amount means an amount of the pharmaceutical agent effective to alleviate or ameliorate the symptoms of an anorectal disorder of the subject being treated.

As the topical disorders are treated with topical compositions of certain fixed concentrations, reference is made herein to "therapeutically effective concentration".

After an initial layer of topical composition has been applied and the solvent has evaporated, providing an initial dried film coating, a second layer may be applied over the initial film. Additional amounts of topical composition can be applied as needed.

In an embodiment, a topical composition is employed to form a coating of less than about 0.5 mm thick. In an embodiment, a topical composition is employed to form a coating of at least about 0.1 mm thick. Such coatings can be formed by applying, for example, about 0.02 ml of topical composition per square centimeter of affected surface area.

In general, the particular length of time required for film formation will vary depending on factors such as the amount of composition applied, the temperature of the rectal or anal mucosal area, the moisture content of the rectal or anal, the surface area for composition application, and the like. However, in an embodiment, film formation is generally complete within about 10 to about 60 seconds. During this period, the person to whom application of the topical composition has been made typically minimizes actions and body movements thus allowing the composition to form a dried film coating.

The topical compositions of the present invention typically act at temperatures between room temperature (20° C.) and body temperature (37° C.). The dried films are conformable and comfortable and may be elastic and flexible, and do not irritate the skin and mucous membrane during the application and in use after drying. The dried films are typically substantially painless and easily removable substantially without pain. The dried films formed from the topical compositions are also typically substantially non-water sensitive and waterproof. The dried films formed from the topical compositions comprise finely-dispersed pharmaceutical ingredients, which can be gradually released to the adhesion area.

The compositions of the present invention are applicable to both human patients and to non-human mammalian subjects such as in veterinary use, for example for treatment of canine, feline, equine, bovine, porcine and primate species.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples illustrate certain embodiments of the invention but are not meant to limit the scope of the claims in any way. The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Table 1 summarizes various embodiments of topical compositions of the present invention in the form of an oil-in-water emulsion liquid prepared for use in treating hemorrhoids.

TABLE 1

| Ingredient | \multicolumn{10}{c}{g per 100 g product} | | | | | | | | | |
|---|---|---|---|---|---|---|---|---|---|---|
| | A | B | C | D | E | F | G | H | H1 | H2 |
| Trimethylsiloxysilicate | 15 | 15 | 15 | 15 | 20 | 20 | 13 | 15 | 25 | 25 |
| Hexamethyldisiloxane | 22 | 22 | 22 | 22 | 24 | 26 | 18 | 43 | | |
| Isooctane | 21 | 21 | 21 | 22.5 | 20 | 20 | 17 | | | |
| Methylsiloxane (0.65 cP) | | | | | | | | | 38.25 | 46.74 |
| Cetyl PEG/PPG-10/1 Dimethicone | 4 | 4 | 4 | | 4 | | 4 | 4 | 4 | 4 |
| Tween 80 | 1.5 | | | | 1.5 | | 1.5 | 1.5 | 1.5 | 3 |
| Tween 20 | | 2 | | | | | | | | |
| Sodium Lauryl Sulfate | | | 1.5 | 3 | | 3 | | | | |
| Water | 25 | 24.5 | 25 | 25 | 30 | 30 | 35 | 25 | | |
| Acetate Buffer pH 4.4 | | | | | | | | | 30 | 20 |
| Pramoxine HCl | 1 | 1 | 1 | 1 | 1 | 1 | 1 | 1 | 1 | 1 |
| Phenylephrine HCl | 0.25 | 0.25 | 0.25 | 0.25 | 0.25 | 0.25 | 0.25 | 0.25 | 0.25 | 0.25 |
| Bis-vinyldimethicone | 5 | 5 | 5 | 5 | | | 5 | 5 | | |
| Vinyldimethicone and hydrogen dimethicone | 5 | 5 | 5 | 5 | | | 5 | 5 | | |
| Cyclopentasiloxane and dimethicone blend | 1 | 1 | 1 | 1 | | | 1 | 1 | | |
| Pemulen TR-1 | | | | | | | | | | 0.01 |

EXAMPLE 2

Composition H1 of Example 1 was prepared as follows:

Trimethylsiloxysilicate powder was dissolved in methylsiloxane at room temperature. Cetyl PEG/PPG-10/1 Dimethicone was added to solution of trimethylsiloxy silicate. Pramoxine and phenylephrine were dissolved in water. The pH of the aqueous solution was adjusted to 4.2-4.4 by acetate buffer. Tween 80 was added to the aqueous solution. The trimethylsiloxysilicate solution was combined with the aqueous solution and mixed by means of a homogenizer at room temperature.

The obtained topical liquid solution was applied to a wipe substrate and sealed to provide a sealed package of single-use wipe impregnated with the topical liquid composition. The composition is applied using single use wipe, wiping the anal region of an adult subject suffering from external hemorrhoids.

EXAMPLE 3

Table 2 summarizes various embodiments of topical compositions of the present invention in the form of a gel for treatment of hemorrhoids.

TABLE 2

| Ingredient | \multicolumn{4}{c}{g per 100 g product} | | | |
|---|---|---|---|---|
| | I | J | K | L |
| Trimethylsiloxysilicate | 15 | 17 | 20 | 25 |
| Hexamethyldisiloxane | 18 | 18 | 21 | |
| Methylsiloxane (0.65 cP) | | | | 42.65 |
| Isooctane | 19 | 20 | 22 | |
| Cetyl PEG/PPG-10/1 Dimethicone | 4 | | 4 | 4 |
| Tween 80 | 1.5 | | 1.5 | 1.5 |
| Sodium Lauryl Sulfate | | 3 | | |
| Water | 30 | 30 | 30 | 25 |
| Pramoxine HCl | 1 | 1 | 1 | 1 |
| Phenylephrine HCl | 0.25 | 0.25 | 0.25 | 0.25 |
| Bis-vinyldimethicone | 5 | 5 | | |

TABLE 2-continued

| Ingredient | \multicolumn{4}{c}{g per 100 g product} | | | |
|---|---|---|---|---|
| | I | J | K | L |
| Vinyldimethicone and hydrogen dimethicone | 5 | 5 | | |
| Cyclopentasiloxane and dimethicone blend | 1 | 1 | | |
| Hydroxypropyl methylcellulose | 0.5 | 0.5 | 0.5 | |
| Hydroxyethylcellulose (Natrosol HHX) | | | | 0.6 |

EXAMPLE 4

Composition L was prepared as follows:

Trimethylsiloxysilicate powder was dissolved at RT in methylsiloxane. Silicon Surfactant Cetyl PEG/PPG-10/1 Dimethicone was added to a solution of Trimethylsiloxysilicate. Pramoxine and phenylephrine were dissolved in water. The pH of the aqueous solution was adjusted to 4.2-4.4 by an acetate buffer. Tween 80 was added to the aqueous solution with slow mixing to avoid bubbling. Hydroxyethylcellulose (Natrosol HHX) was dispersed in the aqueous phase under intensive mixing and heating up to 70 deg C. After the mixture was formed, the mixing was continued until it cooled to room temperature. The trimethylsiloxysilicate solution was combined with the aqueous solution and mixed in a homogenizer at room temperature. Upon dissolution of hydroxypropyl methylcellulose in the aqueous phase, a viscous gel was formed.

The viscous topical gel composition obtained had a viscosity ranging from 25000-45000 cP.

EXAMPLE 5

A female patient aged 42 applied the gel composition L of Table 2, Example 3 on the elbow, neck and internal part of the arm. Shortly thereafter (about 20 seconds) the composition dried and left a thin film on the skin.

The films were examined after 12, 18 and 24 hrs for durability and flexibility. During this period the patient carried out their usual daily activities and took one shower. It was found that the films were durable and remained intact after 12, 18 and 24 hrs.

The films did not fall off the body surface and did not crack or flake off. It was found that the films remained flexible after 12, 18 and 24 hrs. The films closely followed the patient's skin irregularities as well as skin movement throughout the day during normal activity. The skin under the film was slightly pale, which shows the vasoconstrictor phenylephrine was still active after 24 hrs. After 24 hrs, the film was removed from the skin and tested by high performance liquid chromatography (HPLC), whereupon significant amounts of the two actives (pramoxine and phenylephrine) were found in the film despite the extended period of time.

EXAMPLE 6 (Prophetic)

Durability of Films Obtained on Drying of the Compositions of the Present Disclosure A test will be conducted to assess durability of dried films of the present disclosure. The model will be based on the principle that efficacious films provide a physical barrier between the skin and the external environment. Therefore, the film should also prevent wash-off and wear-off of a harmless inert marker substance. Activated carbon powder (ACP) is one such marker.

Film performance will be assessed by randomly applying films of the present disclosure over uniformly made ACP prepared sites on the backs of healthy adult subjects, and measuring the amount of ACP remaining on those sites over a wear period (e.g., one-day period, two-day period, three-day period or more). Subjects will go about normal daily activities and will be asked to shower once per day and avoid excessive physical activity or prolonged water exposure. On a daily basis, standardized digital photographs will be taken of the test sites and used to monitor the amount of ACP remaining using computer-assisted image analysis. The amount of marker stain (ACP) remaining after 1, 2, and 3 days of wear will be used as a measure of film effectiveness. The more stain remaining, the more effective the film at protecting the test site. The results can be presented as a chart of mean±SEM durability expresses as a percentage of the original ACP marker on Day 0.

EXAMPLE 7 (Prophetic)

Flexibility of Films Obtained on Drying of the Compositions of the Present Disclosure A test will be conducted to assess flexibility of dried films of the present disclosure. The films will be prepared on synthetic skin and bent over three sized mandrel bend rods (½", ¼", ⅛") based on ASTM method D4338-97. Multiple data points will be collected for each film. Whether or not the film cracked during the bending process will be recorded.

A tattoo practice skin (synthetic skin) coated with a film of the present disclosure. The skin will be folded to form an inverted U-shaped angle over the mandrel maintaining intimate contact with the upper surface of the film. Using a fresh specimen for each test, the test will be repeated with progressively smaller diameter mandrels.

Procedure:
1) Film will be applied onto tattoo practice skin with a dimension of 2×4 inches.
2) The test films and the test apparatus will be stored at the test conditions for 24 hours.
3) The tests will be run in the same environment used to condition the test films and test apparatus.
4) The largest diameter mandrel will be positioned in the horizontal operating position in the test frame.
5) The test film will be grasped between the thumb and forefinger of one hand, with the longest dimensions between the fingers. For low-temperature testing, a cotton work glove can be used to insulate the test film from the warm fingers.
6) A flat steel (or other support structure) of the test film will be laid tangentially at right angles to the longitudinal axis of the test mandrel.
7) The test film will be folded with the lower surface opposite to the mandrel to form an inverted U-shaped angle over the mandrel maintaining intimate contact with the mandrel.
8) Any fracture, crazing, or cracking of the film, observed with the naked eye, will be recorded.
9) A fresh film will be folded onto the next smaller diameter mandrel.
10) The test will be repeated a number of times, using fresh films, on three mandrels with different diameters.
11) Flexibility of the films will be determined by the ability of the films to not crack when subjected to bending.

EXAMPLE 8

Efficacy of Compositions of the Present Invention in the Treatment Of Hemorrhoids Background: In a randomized clinical study, patients were divided into 3 groups and received either PP-110 gel (composition L in Table 2), PP-110 wipes (composition H1 in Table 1) or Preparation-H® cream as a comparator. PP-110 was applied once daily, while Preparation-H was applied 4 times a day, as indicated.

All patients were asked to record parameters such as pain, bleeding, itching, swelling, discomfort, and mucus discharge over a period of 14 days while using the assigned treatment. For most parameters, patients were asked to choose between 0=none, 1=mild, 2=moderate and 3=significant for each day. The only exception was pain, where they were asked to select a pain level between 1=none to 10=maximal.

Results: Based on the first 32 patients who completed the protocol (9 of them with PP-110 gel, 11 with PP-110 wipes, and 12 with Preparation-H cream), the following interim results were obtained:

Pain: Reported pain, throughout the 14 days of treatment for PP-110 (gel or wipes) was reduced compared to reported pain in the Preparation-H arm, even though PP-110 was used once daily and Preparation-H was used 4 times per day. FIG. 1 shows hemorrhoidal pain level after treatment with compositions of the present invention as gel and wipes, as compared to Preparation H. The data presented are the delta meaning the change from the previous day for each parameter measured.

Figure 2:
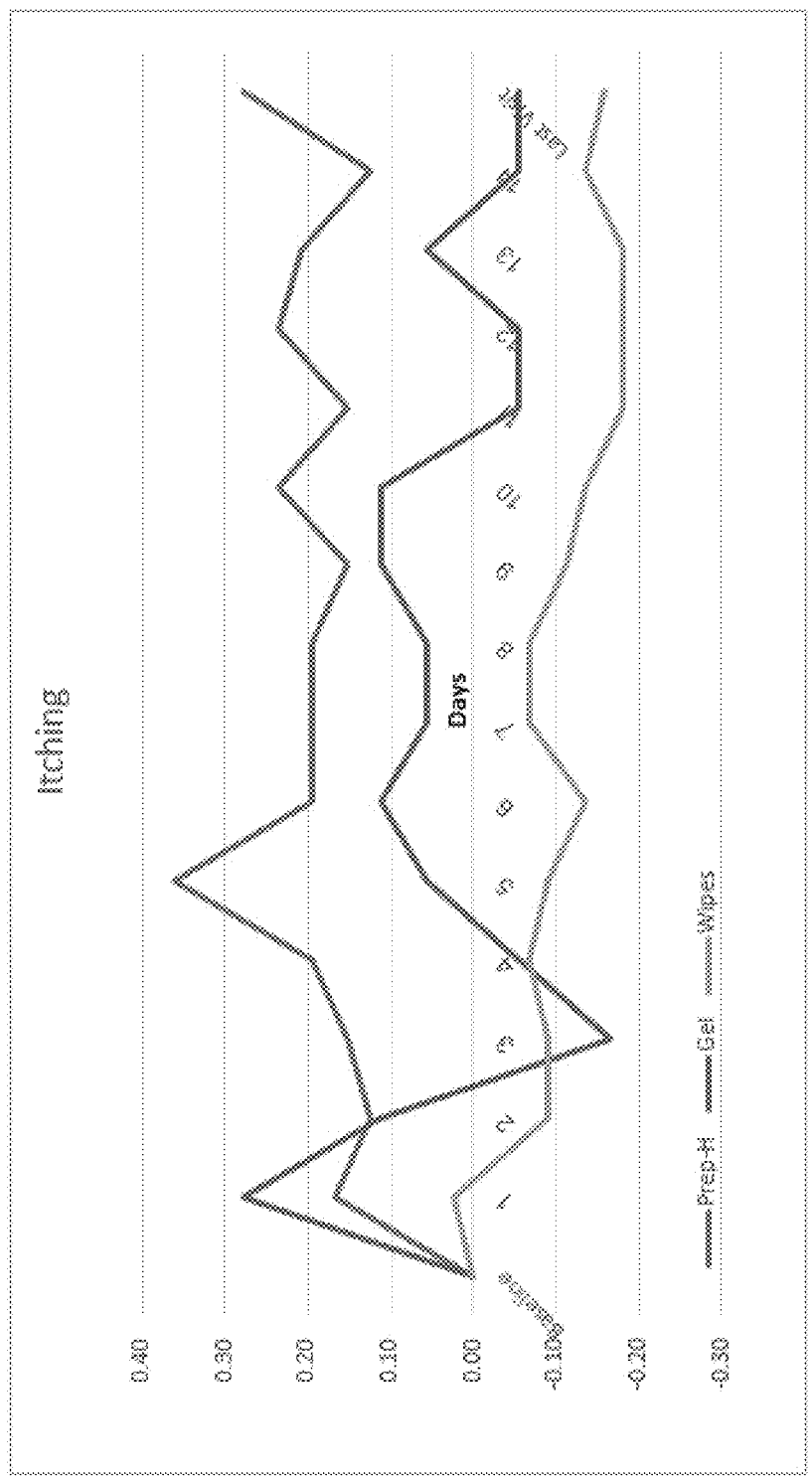
FIG. 2 shows hemorrhoidal itching after treatment with compositions of the present invention as gel and wipes as compared to Preparation H. The data presented are the delta meaning the change from the previous day for each parameter measured.

Itching: Itching, throughout the 14 days of treatment for PP-110 (gel or wipes) was significantly reduced compared to reported itching in the Preparation-H arm. FIG. 2 shows hemorrhoidal itching after treatment with compositions of the present invention as gel and wipes as compared to Preparation H. The data presented are the delta meaning the change from the previous day for each parameter measured.

Figure 3:
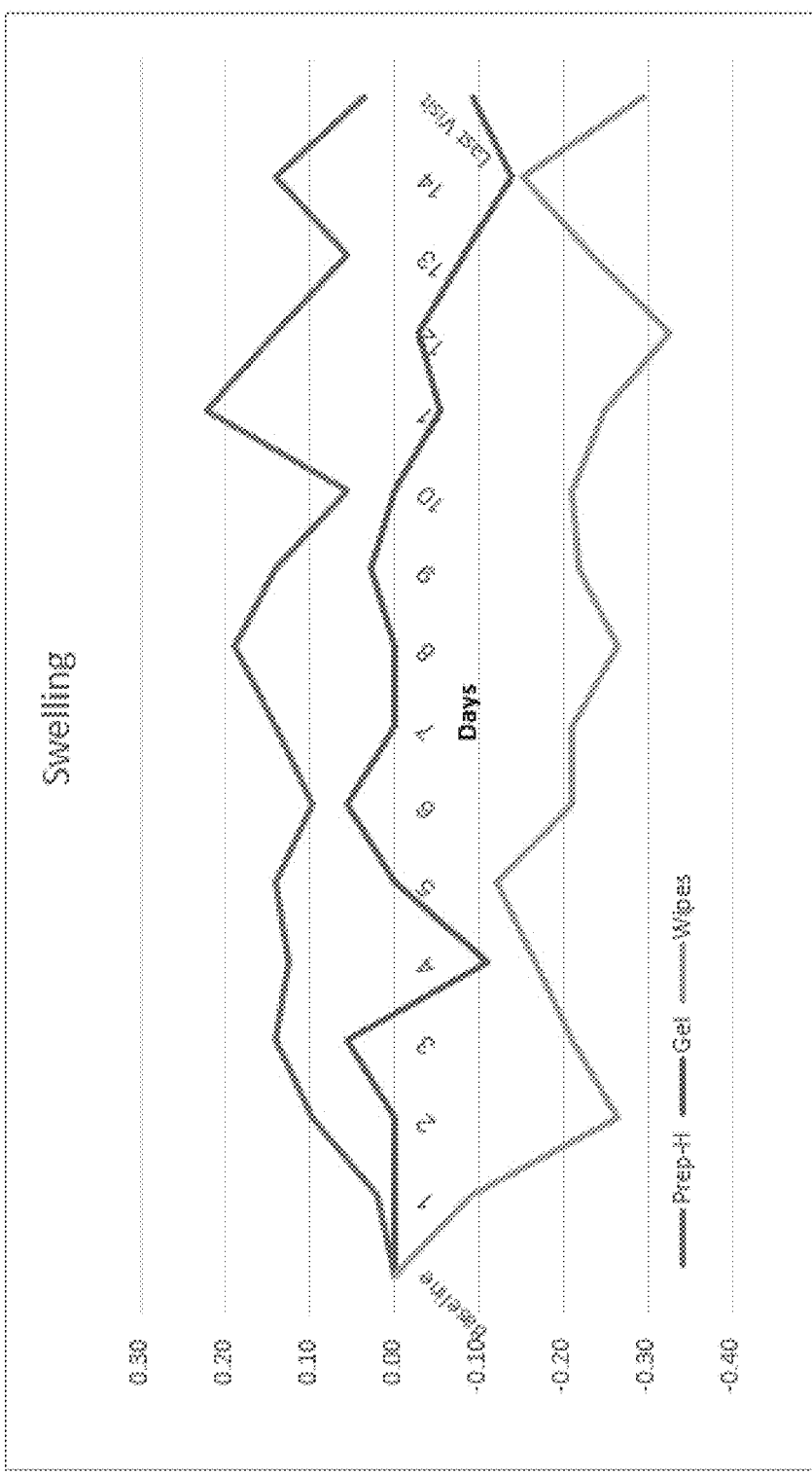
FIG. 3 shows hemorrhoidal swelling after treatment with compositions of the present invention as gel and wipes, as compared to Preparation H. The data presented are the delta meaning the change from the previous day for each parameter measured.

Swelling: For swelling values for the PP-110 gel and wipe arms throughout the 14 days of treatment were significantly reduced compared to reported swelling in the Preparation-H arm. FIG. 3 shows hemorrhoidal swelling after treatment with compositions of the present invention as gel and wipes, as compared to Preparation H. The data presented are the delta meaning the change from the previous day for each parameter measured.

Figure 4:
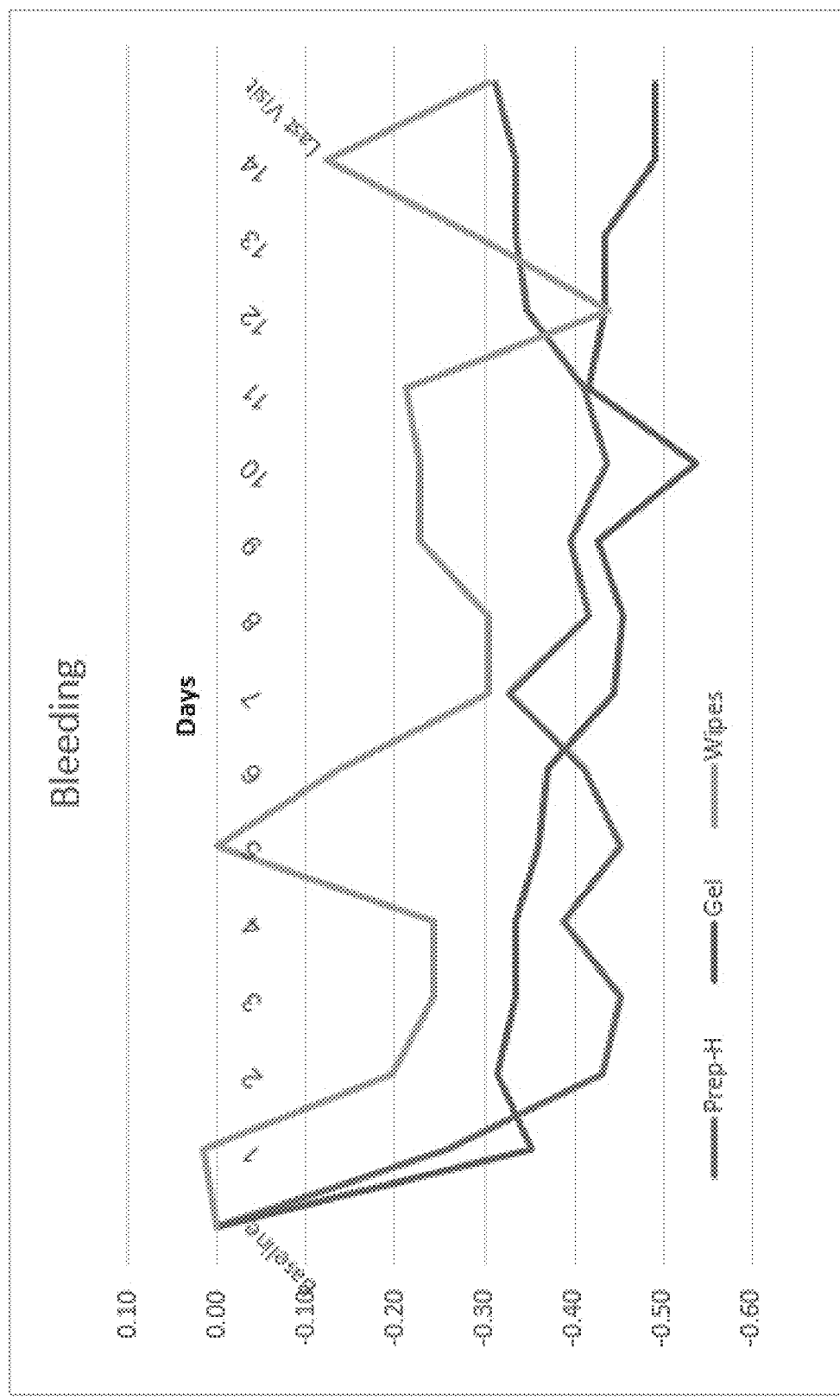
FIG. 4 shows hemorrhoidal bleeding after treatment with compositions of the present invention as gel and wipes, as compared to Preparation H. The data presented are the delta meaning the change from the previous day for each parameter measured.

Bleeding: PP-110 gel patients and Preparation-H patients showed similar bleeding results throughout the 14 days. PP-110 wipe patients were slightly behind in the first 7 days of treatment, but caught on after that. FIG. 4 shows hemorrhoidal bleeding after treatment with compositions of the present invention as gel and wipes, as compared to Preparation H. The data presented are the delta meaning the change from the previous day for each parameter measured.

Figure 5:
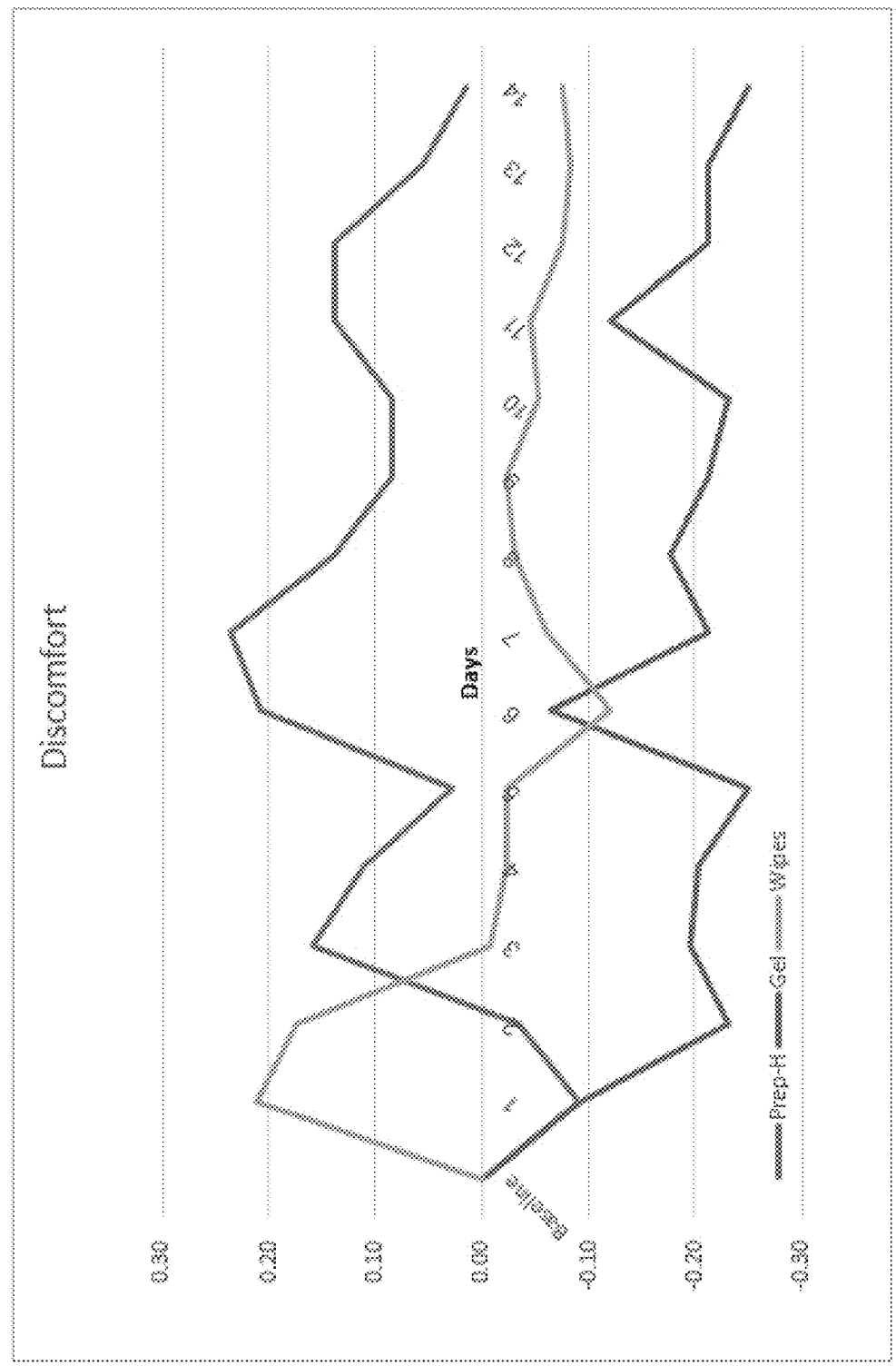
FIG. 5 shows hemorrhoidal discomfort after treatment with compositions of the present invention as gel and wipes, as compared to Preparation H. The data presented are the delta meaning the change from the previous day for each parameter measured.

Discomfort: Results of all 3 arms with respect to discomfort were comparable, even though PP-110 patients used the product once daily and Preparation-H patients—4 times a day. FIG. 5 shows hemorrhoidal discomfort after treatment with compositions of the present invention as gel and wipes, as compared to Preparation H.

Summary: In all clinical parameters one or both of PP-110 arms showed comparable or superior results compared to the Preparation-H arm. This includes pain, itching, swelling, bleeding and discomfort, and was achieved even though PP-110 was applied once daily and Preparation-H was applied 4 times per day. The data presented are the delta meaning the change from the previous day for each parameter measured.

EXAMPLE 9

Liquid Compositions with Pemulen TR-1 for the Preparation of Wipes

Composition H2 of Table 1 in Example 1 was prepared similarly to composition H1, with added Pemulen TR-1:

Trimethylsiloxysilicate powder was dissolved in methylsiloxane at room temperature. Cetyl PEG/PPG-10/1 Dimethicone was added to solution of trimethylsiloxy silicate. Pramoxine and phenylephrine were dissolved in water. The pH of the aqueous solution was adjusted to 4.2-4.4 by acetate buffer. Tween 80 was added to the aqueous solution. The trimethylsiloxysilicate solution was combined with the aqueous solution and mixed by means of a homogenizer at room temperature.

A topical liquid composition was obtained, whose viscosity ranges from 1-1.2 cP, close to the viscosity of water.

The obtained topical liquid composition was applied to a wipe substrate and sealed to provide a sealed package of single-use wipe impregnated with the topical liquid composition. The composition is applied using single use wipe, wiping the anal region of an adult subject suffering from external hemorrhoids.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A topical composition comprising:
   from 15.0% (w/w) to 25.0% (w/w) of trimethylsiloxysilicate;
   from 1.0% (w/w) to 5% (w/w) of at least one surfactant;
   at least 15% (w/w) water;
   from 30.0% (w/w) to 50% (w/w) of methylsiloxane; and
   a therapeutically effective concentration of at least one pharmaceutical agent selected from the group consisting of pramoxine, phenylephrine, hydrocortisone, salicylic acid, nitroglycerine, sildenafil, nifedipine, verapamil, diltiazem, procaine, lidocaine, tetracaine, dibucaine, prilocaine, phenacaine, benzyl alcohol, benzocaine, diperodon, dyclonine, dimethisoquin, epinephrine, tetrahydrozoline hydrochloride, an amphetamine, an antihistamine, methylphenidate, mephedrone, oxymetazoline, pseudoephedrine, psilocybin, ephedrine sulphate, imiquimod, podophyllin, podophylotoxin, fluorouracil, sinecatechins, plant extracts, adapalene, benzoyl peroxide, tazarotene, azelaic acid, clindamycin, acyclovir, penciclovir, famciclovir, docosanol, diclofenac, or their salts and combinations thereof,
   wherein the composition is sufficiently designed to dry within 60 seconds after application to a body surface to form a dried composition, and wherein the dried composition forms:
   (i) a flexible film, wherein the flexible film closely follows irregularities of the body surface as well as movement of the body surface, and
   (ii) a durable film, wherein the durable film does not crack or flake off and remains intact for more than 12 hours giving release of the pharmaceutical agent for an extended period of time.

2. The composition of claim 1 being substantially non-stinging.

3. The composition of claim 1 in the form of a gel.

4. The composition of claim 1 in the form of an oil-in-water emulsion.

5. The composition of claim 1 wherein the at least one surfactant is a polysorbate.

6. The composition of claim 5 wherein the polysorbate is polyoxyethylene sorbitan monooleate.

7. The composition of claim 1 further comprising an additive selected from the group consisting of a dimethicone/vinyl dimethicone crosspolymer, a silicone gum blend, a gelling agent, and a combination thereof.

8. The composition of claim 1 comprising from 15% (w/w) to 40% (w/w) of water.

9. The composition of claim 1 further comprising a buffer to adjust the pH of the composition to a pH value between 4.2-4.4.

10. The composition of claim 1 further comprising an organosilicone surfactant.

11. The composition of claim 10 wherein the organosilicone surfactant is a cetyl dimethicone copolyol.

12. The composition of claim 10 further comprising a viscosity modifier.

13. A method of treating an anorectal disorder comprising topically applying once daily to the mucosal surface of an anorectal region of a subject in need of such treatment a therapeutically effective amount of the composition of claim 1.

14. The method of claim 13 wherein, after a period of time post topical application of the composition, a similar or better therapeutic effect is observable than a commercially available composition comprising the same active ingredient(s) in the same concentrations wherein applied several times daily.

15. The method of claim 13 wherein the anorectal disorder is hemorrhoids.

16. A method of treating an anorectal disorder comprising topically applying once every other day to the mucosal surface of an anorectal region of a subject in need of such treatment a therapeutically effective amount of the composition of claim 1.

17. The method of claim 16 wherein, after a period of time post topical application of the composition, a similar or better therapeutic effect is observable than a commercially available composition comprising the same active ingredient(s) in the same concentrations wherein applied several times daily.

18. The method of claim 16 wherein the anorectal disorder is hemorrhoids.

19. A method of treating an anorectal disorder comprising topically applying twice weekly to the mucosal surface of an anorectal region of a subject in need of such treatment a therapeutically effective amount of the composition of claim 1.

20. The method of claim 19 wherein, after a period of time post topical application of the composition, a similar or better therapeutic effect is observable than a commercially available composition comprising the same active ingredient(s) in the same concentrations wherein applied several times daily.

21. The method of claim 19 wherein the anorectal disorder is hemorrhoids.

22. A kit comprising the composition of claim 1 and a container-applicator device suitable for storage and application of the composition to a body surface.

23. The kit according to claim 22 wherein the container-applicator device is selected from the group consisting of a single use wipe, a syringe, a dropper, a spray dispenser, a compressible bottle or tube, a spatula, a suppository insertion tube, an extrusion tube, and an inflatable member.

* * * * *